(12) United States Patent
Tojo et al.

(10) Patent No.: US 9,573,923 B2
(45) Date of Patent: *Feb. 21, 2017

(54) LIQUID CRYSTAL COMPOUND HAVING 2, 6-DIFLUOROPHENYLETHER STRUCTURE, AND LIQUID CRYSTAL COMPOSITION CONTAINING THE SAME

(71) Applicant: DIC CORPORATION, Tokyo (JP)

(72) Inventors: Kenta Tojo, Kita-adachi-gun (JP); Tetsuo Kusumoto, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/907,034

(22) PCT Filed: Aug. 28, 2014

(86) PCT No.: PCT/JP2014/072633
§ 371 (c)(1),
(2) Date: Jan. 22, 2016

(87) PCT Pub. No.: WO2015/049940
PCT Pub. Date: Apr. 9, 2015

(65) Prior Publication Data
US 2016/0159765 A1 Jun. 9, 2016

(30) Foreign Application Priority Data

Oct. 3, 2013 (JP) ................................. 2013-208200

(51) Int. Cl.
| | |
|---|---|
| *C07D 319/06* | (2006.01) |
| *C07D 309/06* | (2006.01) |
| *C09K 19/20* | (2006.01) |
| *C09K 19/32* | (2006.01) |
| *C09K 19/04* | (2006.01) |
| *C09K 19/30* | (2006.01) |
| *C09K 19/34* | (2006.01) |

(52) U.S. Cl.
CPC ........... *C07D 319/06* (2013.01); *C07D 309/06* (2013.01); *C09K 19/04* (2013.01); *C09K 19/20* (2013.01); *C09K 19/3066* (2013.01); *C09K 19/322* (2013.01); *C09K 19/3402* (2013.01); *C09K 2019/3422* (2013.01)

(58) Field of Classification Search
CPC .................................................... C07D 319/06
USPC ....................................................... 549/374
See application file for complete search history.

(56) References Cited

U.S. PATENT DOCUMENTS

| | | | |
|---|---|---|---|
| 5,032,313 A | 7/1991 | Goto et al. | |
| 5,324,449 A | 6/1994 | Kurmeier et al. | |
| 5,487,845 A | 1/1996 | Reiffenrath et al. | |
| 6,200,654 B1 | 3/2001 | Poetsch et al. | |
| 6,210,603 B1 | 4/2001 | Kondo et al. | |
| 6,579,577 B2 | 6/2003 | Kondo et al. | |
| 8,916,718 B2* | 12/2014 | Tojo ........................ | C09K 19/20 549/370 |
| 9,079,836 B2* | 7/2015 | Tojo ...................... | C09K 19/062 |
| 9,181,484 B2* | 11/2015 | Tojo ........................ | C09K 19/20 |
| 9,315,727 B2* | 4/2016 | Tojo ........................ | C07C 43/225 |
| 2002/0166994 A1 | 11/2002 | Kondo et al. | |
| 2003/0236304 A1 | 12/2003 | Jolidon et al. | |
| 2005/0017216 A1 | 1/2005 | Poetsch et al. | |
| 2005/0092966 A1 | 5/2005 | Heckmeier et al. | |

(Continued)

FOREIGN PATENT DOCUMENTS

| | | |
|---|---|---|
| CN | 102186821 A | 9/2011 |
| JP | 2-501311 A | 5/1990 |

(Continued)

OTHER PUBLICATIONS

International Search Report dated Oct. 7, 2014, issued in counterpart Application No. PCT/JP2014/072633 (3 pages).

(Continued)

*Primary Examiner* — Nizal Chandrakumar
(74) *Attorney, Agent, or Firm* — Westerman, Hattori, Daniels & Adrian, LLP

(57) ABSTRACT

The present invention relates to a compound having a 2,6-difluorophenylether structure useful as organic electronic materials, pharmaceuticals and agrochemicals, and in particular, liquid crystal display device materials. Provided are a compound represented by general formula (1):

$$R-(A^1-Z^1)_m-(A^2-Z^2)_n-(A^3-Z^3)_p-\text{Ar}-(A^4-Z^4)_r-(A^5-Z^5)_s-A^6 \quad (1)$$

and a liquid crystal composition containing the compound and a liquid crystal display device that uses the liquid crystal composition.

Since the compound represented by general formula (1) is used as a component of a liquid crystal composition, a liquid crystal composition that exhibits low viscosity and a liquid crystal phase over a wide temperature range can be obtained. Thus, the compound is particularly useful as a component of a liquid crystal composition for high-response-speed liquid crystal display devices.

9 Claims, 1 Drawing Sheet

(56) References Cited

U.S. PATENT DOCUMENTS

| | | |
|---|---|---|
| 2006/0263542 A1 | 11/2006 | Kirsch et al. |
| 2007/0051919 A1 | 3/2007 | Kondou et al. |
| 2009/0065739 A1 | 3/2009 | Haseba et al. |
| 2009/0302273 A1 | 12/2009 | Tanaka |
| 2010/0127211 A1 | 5/2010 | Tanaka |
| 2010/0328600 A1 | 12/2010 | Shimada et al. |
| 2011/0193022 A1 | 8/2011 | Tanaka et al. |

FOREIGN PATENT DOCUMENTS

| | | |
|---|---|---|
| JP | 2-233626 A | 9/1990 |
| JP | 4-501575 A | 3/1992 |
| JP | 6-504032 A | 5/1994 |
| JP | 9-157202 A | 6/1997 |
| JP | 10-101599 A | 4/1998 |
| JP | 2000-355560 A | 12/2000 |
| JP | 2001-019649 A | 1/2001 |
| JP | 2004-352721 A | 12/2004 |
| JP | 2004-355560 A | 12/2004 |
| JP | 2005-517079 A | 6/2005 |
| JP | 5-263461 B2 | 8/2013 |
| JP | 2013-170246 A | 9/2013 |
| JP | 5-382268 B1 | 1/2014 |
| JP | 5435318 B1 | 3/2014 |
| JP | 2014-105178 A | 6/2014 |
| KR | 10-2006-0119879 A | 11/2006 |
| WO | 98/23564 A1 | 6/1998 |
| WO | 2005/019377 A1 | 3/2005 |
| WO | 2008/105286 A1 | 9/2008 |
| WO | 2010/047260 A1 | 4/2010 |
| WO | 2012/161178 A1 | 11/2012 |
| WO | 2013/018796 A1 | 2/2013 |
| WO | 2013/099754 A1 | 7/2013 |
| WO | 2013/141116 A1 | 9/2013 |
| WO | 2013/172162 A1 | 11/2013 |

OTHER PUBLICATIONS

Written Opinion dated Oct. 7, 2014, issued in counterpart Application No. PCT/JP2014/072633 (5 pages).
Notification of Reasons for Refusal dated Jan. 29, 2015, issued in counterpart Japanese Patent Application No. 2014-556869, w/English translation (6 pages).
Decision to Grant a Patent dated Apr. 2, 2015, issued in counterpart Japanese Patent Application No. 2014-556869, w/English translation (5 pages).
International Search Report dated Aug. 6, 2013, issued in PCT/JP2013/062077.
International Search Report dated Dec. 10, 2013, issued in counterpart Application No. PCT/JP2013/075266.
Written Opinion dated Dec. 10, 2013, issued in counterpart Application No. PCT/JP2013/075266.
International Search Report dated Apr. 2, 2013, issued in counterpart Application No. PCT/JP2012/083070.
Kuchar, Miroslav, et al., "Use of QSAR in Design of Antiinflammatory Fluorinated Arylalkanoic Acids", Collection of Czechoslovak Chemical Communications, 1990, vol. 55, No. 1, pp. 296-306.
Resistry(stn) [Online], Oct. 3, 2011 (Oct. 3, 2011), (retrieval date: Mar. 11, 2013 (Mar. 11, 2013)) CAS resistration No. 1334226-61-7.
International Search Report dated Oct. 7, 2014, issued in counterpart Application No. PCT/JP2014/068784.
Written Opinion dated Oct. 7, 2014, issued in counterpart Application No. PCT/JP2014/068784.
Notification of Reasons for Refusal dated Jan. 29, 2015, issued in counterpart Japanese Patent Application No. 2014-556873, w/English translation.

\* cited by examiner

LIQUID CRYSTAL COMPOUND HAVING 2, 6-DIFLUOROPHENYLETHER STRUCTURE, AND LIQUID CRYSTAL COMPOSITION CONTAINING THE SAME

TECHNICAL FIELD

The present invention relates to a compound having a 2,6-difluorophenylether structure useful as organic electronic materials, pharmaceuticals and agrochemicals, and in particular, liquid crystal display device materials.

BACKGROUND ART

Liquid crystal display devices are being used in watches, calculators, various measurement instruments, automobile panels, word processors, electronic organizers, printers, computers, televisions, clocks, advertising boards, etc. Representative examples of liquid crystal display modes are twisted nematic (TN) mode, super twisted nematic (STN) mode, and vertical alignment (VA) or in-plane-switching (IPS) mode that uses thin film transistors (TFTs). The liquid crystal compositions used in these liquid crystal display devices are required to be stable against external factors such as moisture, air, heat, and light, exhibit a liquid crystal phase (nematic phase, smectic phase, or blue phase, for example) in a temperature range as wide as possible around room temperature, have low viscosity, and operate at low drive voltage. The liquid crystal compositions are composed of several to dozens of compounds in order to optimize dielectric anisotropy (Δ∈), refractive index anisotropy (Δn), etc., for each individual display device.

Horizontal alignment displays such as TN, STN, or IPS displays use liquid crystal compositions having positive Δ∈. There has been a report of a driving mode with which a liquid crystal composition having a positive Δ∈ is aligned vertically in the absence of voltage and images are displayed by applying a horizontal electric field. The need for liquid crystal compositions having positive Δ∈ has increased as ever. Meanwhile, improvements in response speed are required in all drive modes, and a liquid crystal composition having a viscosity lower than those of the existing products has been pursued to meet this need. In order to obtain a low-viscosity liquid crystal composition, it is effective to lower the viscosity of each polar compound constituting the liquid crystal composition. Increasing Δ∈ of polar compounds used can decrease the ratios of low-viscosity nonpolar compounds added and can thereby decrease the viscosity of the liquid crystal composition. In order to use the liquid crystal composition in a display device or the like, the liquid crystal composition is required to exhibit a stable nematic phase over a wide temperature range. In order to keep a nematic phase over a wide temperature range, each component of the liquid crystal composition is required to have high miscibility with other components.

In general, introducing a large number of polar atoms, such as fluorine atoms and oxygen atoms, is effective for yielding high Δ∈. However, it is known that merely increasing the number of polar groups introduced decreases miscibility with the liquid crystal composition and causes drawbacks such as precipitation. It is believed that, in order to obtain a low-viscosity compound, it is effective to use a compound having plural ring structures, such as 1,4-cyclohexylene groups and 1,4-phenylene groups, directly bonded to one another without any bonding groups, in other words, a directly-bonded-ring compound. However, directly-bonded-ring compounds generally have high crystallinity and poor miscibility with liquid crystal compositions. Compounds having various bonding groups introduced therein are being studied to overcome this problem. It has been made clear that introduction of bonding groups can improve miscibility of the compounds with the liquid crystal compositions (PTL 1 to PTL 8). The following compound is a compound disclosed as having a further lower viscosity and high miscibility with a liquid crystal composition (PTL 9); however, the Δ∈ thereof is not sufficiently large.

[Chem. 1]

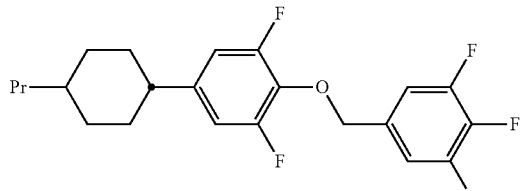

[Chem. 2]

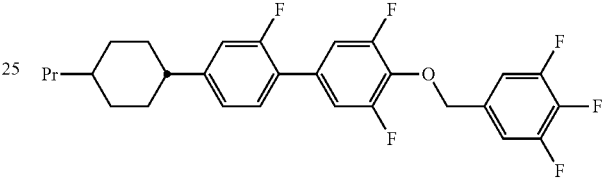

CITATION LIST

Patent Literature

PTL 1: Japanese Unexamined Patent Application Publication No. 10-101599
PTL 2: Japanese Unexamined Patent Application Publication (Translation of PCT Application) No. 2-501311
PTL 3: Japanese Unexamined Patent Application Publication No. 9-157202
PTL 4: Japanese Unexamined Patent Application Publication (Translation of PCT Application) No. 2005-517079
PTL 5: Japanese Unexamined Patent Application Publication No. 2-233626
PTL 6: Japanese Unexamined Patent Application Publication (Translation of PCT Application) No. 4-501575
PTL 7: Japanese Unexamined Patent Application Publication (Translation of PCT Application) No. 6-504032
PTL 8: WO 98/23564
PTL 9: WO 2012/161178

SUMMARY OF INVENTION

Technical Problem

An object of the present invention is to provide a compound that has large Δ∈, low viscosity (η), and high miscibility with other liquid crystal compounds, and to provide a liquid crystal composition and a liquid crystal display device containing the compound.

Solution to Problem

The inventors of the present application have studied various compounds to achieve the object, and have found that a compound that has a 2,6-difluorophenlylether structure and a 1,3-dioxane ring or pyran ring can be used to effectively achieve the object. Thus, the present invention has been made.

The present invention provides a compound represented by general formula (1)

[Chem. 3]

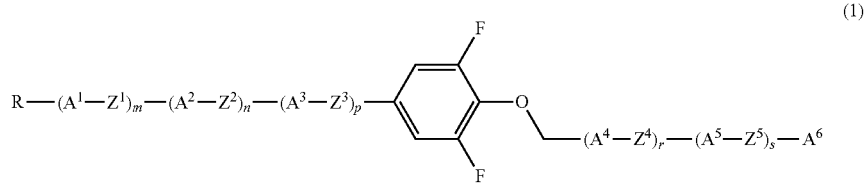

(1)

(where R represents an alkyl group having 1 to 15 carbon atoms or an alkenyl group having 2 to 15 carbon atoms and one —$CH_2$— or two or more non-adjacent —$CH_2$— in the group may each be substituted with —O—, —S—, —COO—, —OCO—, or —CO—, $A^1$, $A^2$, $A^3$, $A^4$, and $A^5$ each independently represent a group selected from the group consisting of (a) a 1,4-cyclohexylene group (one —$CH_2$— or two or more non-adjacent —$CH_2$— in the group may each be substituted with —O— or —S—), (b) a 1,4-phenylene group (one —CH= or two or more non-adjacent —CH= in the group may each be substituted with —N= and a hydrogen atom in the group may be substituted with a fluorine atom), and (c) a naphthalene-2,6-dienyl group (a hydrogen atom in the group may be substituted with a fluorine atom), at least one group selected from $A^1$, $A^2$, and $A^3$ is a group represented by

[Chem. 4]

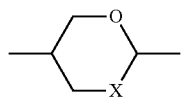

(where X represents an oxygen atom or —$CH_2$—),
$Z^1$, $Z^2$, $Z^3$, $Z^4$, and $Z^5$ each independently represent —$CH_2O$—, —$OCH_2$—, —$CF_2O$—, —$OCF_2$—, —$CH_2CH_2$—, —$CF_2CF_2$—, —CH=CH—, —CF=CF—, —C≡C—, or a single bond,
$A^6$ represents

[Chem. 5]

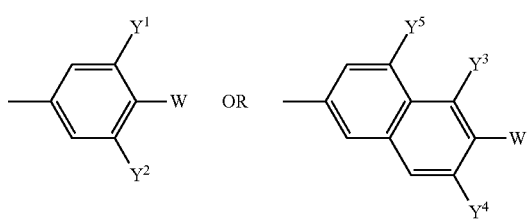

(where W represents a fluorine atom, a chlorine atom, a cyano group, —$CF_3$, —$OCH_2F$, —$OCHF_2$, or —$OCF_3$, and $Y^1$, $Y^2$, $Y^3$, $Y^4$, and $Y^5$ each independently represent a fluorine atom, a chlorine atom, or a hydrogen atom), m, n, p, r, and s each independently represent 0 or 1, at least one selected from m, n, and p represents 1, and m+n+p+r+s equals 1, 2, or 3). In addition, a liquid crystal composition containing this compound and a liquid crystal display device that uses this liquid crystal composition are provided.

Advantageous Effects of Invention

A novel liquid crystal compound represented by general formula (1) provided by the present invention can be easily industrially produced, and the compound represented by general formula (1) obtained has relatively large Δ∈, low viscosity, and high miscibility with a liquid crystal composition.

Thus, when a compound represented by general formula (1) is used as a component of a liquid crystal composition, a liquid crystal composition that has low viscosity and exhibits a liquid crystal phase over a wide range of temperature can be obtained. Accordingly, the compound is highly useful as a component of a liquid crystal composition for a liquid crystal display device required to achieve high response speed.

DESCRIPTION OF EMBODIMENTS

Figure 1:
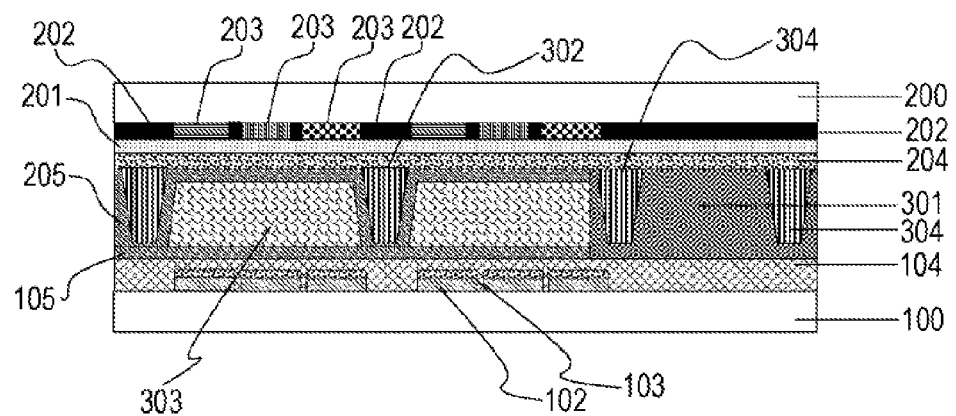
FIG. 1 is a cross-sectional view of a liquid crystal display device according to the present invention, in which a substrate equipped with 100 to 105 is referred to as a "backplane" and a substrate equipped with 200 to 205 is referred to as a "frontplane".
Figure 2:
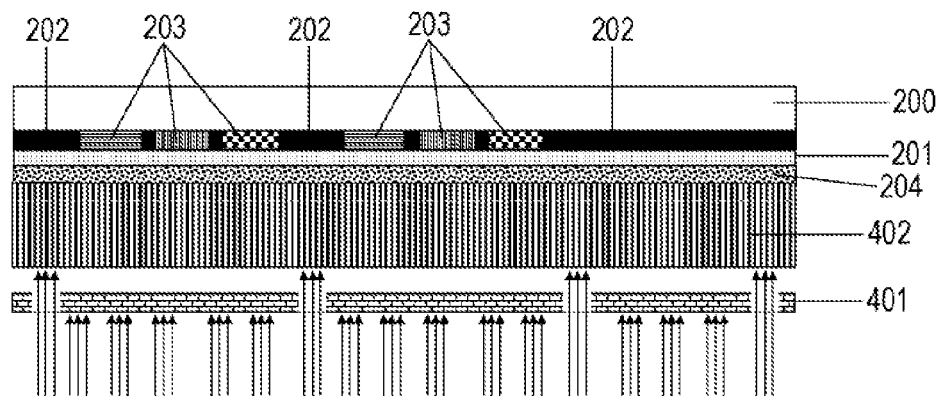
FIG. 2 is a diagram showing an exposure treatment step that uses, as a photomask pattern, a columnar-spacer-forming pattern on a black matrix.

In general formula (1), R preferably represents an alkyl group having 1 to 8 carbon atoms or an alkenyl group having 2 to 8 carbon atoms, and more preferably represents an alkyl group having 1 to 5 carbon atoms or an alkenyl group having 2 to 5 carbon atoms in order to decrease viscosity. R is preferably linear.

In order to decrease viscosity, $A^1$, $A^2$, $A^3$, $A^4$, and $A^5$ preferably each independently represent a trans-1,4-cyclohexylene group, an unsubstituted naphthalene-2,6-diyl group, or an unsubstituted 1,4-phenylene group, and more preferably represent a trans-1,4-cyclohexylene group. In order to increase Δ∈, the followings are preferable:

[Chem. 6]

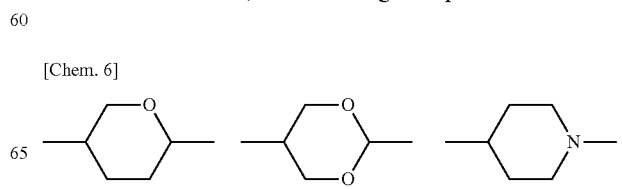

-continued

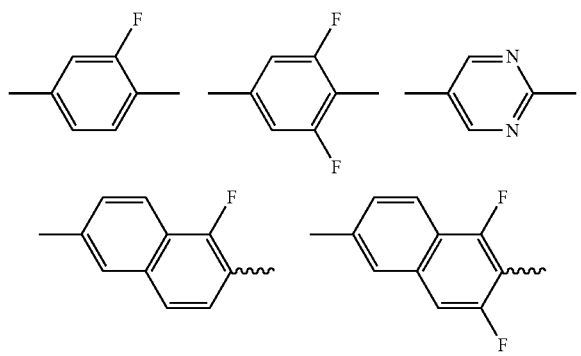

The followings are more preferable:

[Chem. 7]

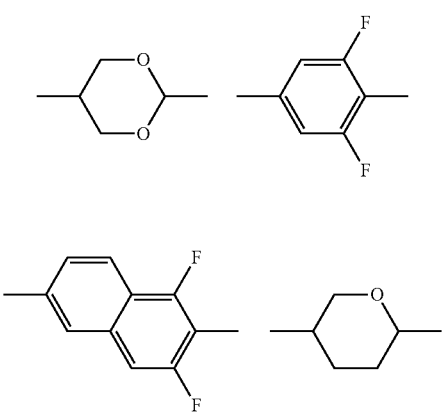

In order to improve long-term reliability of a liquid crystal display device, no nitrogen atoms are preferably contained.

At least one selected from $A^1$, $A^2$, and $A^3$ preferably represents a 1,3-dioxane-2,5-diyl group or a pyran-1,4-diyl group. In order to increase $\Delta\varepsilon$, at least one selected from $A^1$, $A^2$, and $A^3$ preferably represents a 1,3-dioxane-2,5-diyl group.

In order to increase $\Delta\varepsilon$, X preferably represents an oxygen atom and in order to decrease viscosity and increase miscibility with other liquid crystal components, X preferably represents —$CH_2$—.

In order to decrease viscosity, $A^6$ preferably represents the following:

[Chem. 8]

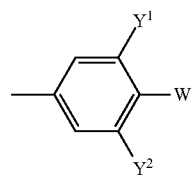

In order to increase $\Delta\varepsilon$,

[Chem. 9]

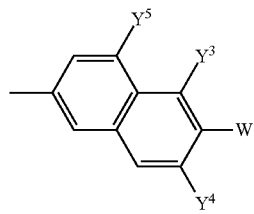

is preferable.

In order to decrease viscosity, $Y^1$, $Y^2$, $Y^3$, $Y^4$, and $Y^5$ preferably each independently represent a hydrogen atom; in order to increase $\Delta\varepsilon$, they preferably each independently represent a fluorine atom; and in order to increase miscibility with other liquid crystal components, they preferably each independently represent a hydrogen atom. When $Y^3$ to $Y^5$ each independently represent a fluorine atom or a hydrogen atom and when the viscosity and miscibility with other liquid crystal components are important, $Y^3$ preferably represents a fluorine atom and $Y^4$ and $Y^5$ each preferably represent a hydrogen atom. In order to increase $\Delta\varepsilon$, $Y^3$ and $Y^4$ each preferably represent a fluorine atom and $Y^5$ preferably represents a fluorine atom or a hydrogen atom.

In order to increase $\Delta\varepsilon$, W preferably represents a fluorine atom, a cyano group, —$CF_3$, or —$OCF_3$, and in order to decrease viscosity, W preferably represents a fluorine atom.

In order to decrease viscosity, $Z^1$, $Z^2$, $Z^3$, and $Z^4$ preferably each independently represent —$CH_2O$—, —$OCH_2$—, —$CF_2O$—, —$OCF_2$—, —$CF=CF$—, —$C_2C$—, or a single bond, more preferably —$CF_2O$—, —$OCF_2$—, —$CH_2CH_2$—, or a single bond, and most preferably a single bond.

When $\eta$ is important, m, n, p, r, and s preferably satisfy m+n+p+r+s=1. In particular, r and s preferably each represent 0. When $T_{ni}$ and $\Delta\varepsilon$ are important, m+n+p+r+s preferably equals 2 or 3. In order to increase miscibility with the liquid crystal composition, m+n+p+r+s preferably equals 1 or 2.

In the compound represented by general formula (1), hetero atoms will not directly bond to one another.

Preferable specific examples of the compound are described below, but the scope of the present invention is not limited by these examples.

Among compounds represented by general formula (1), compounds represented by general formula (1a) to general formula (1f) below are preferable.

[Chem. 10]

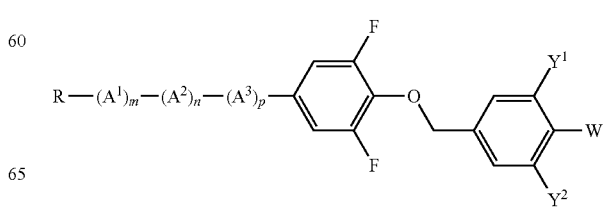

(1a)

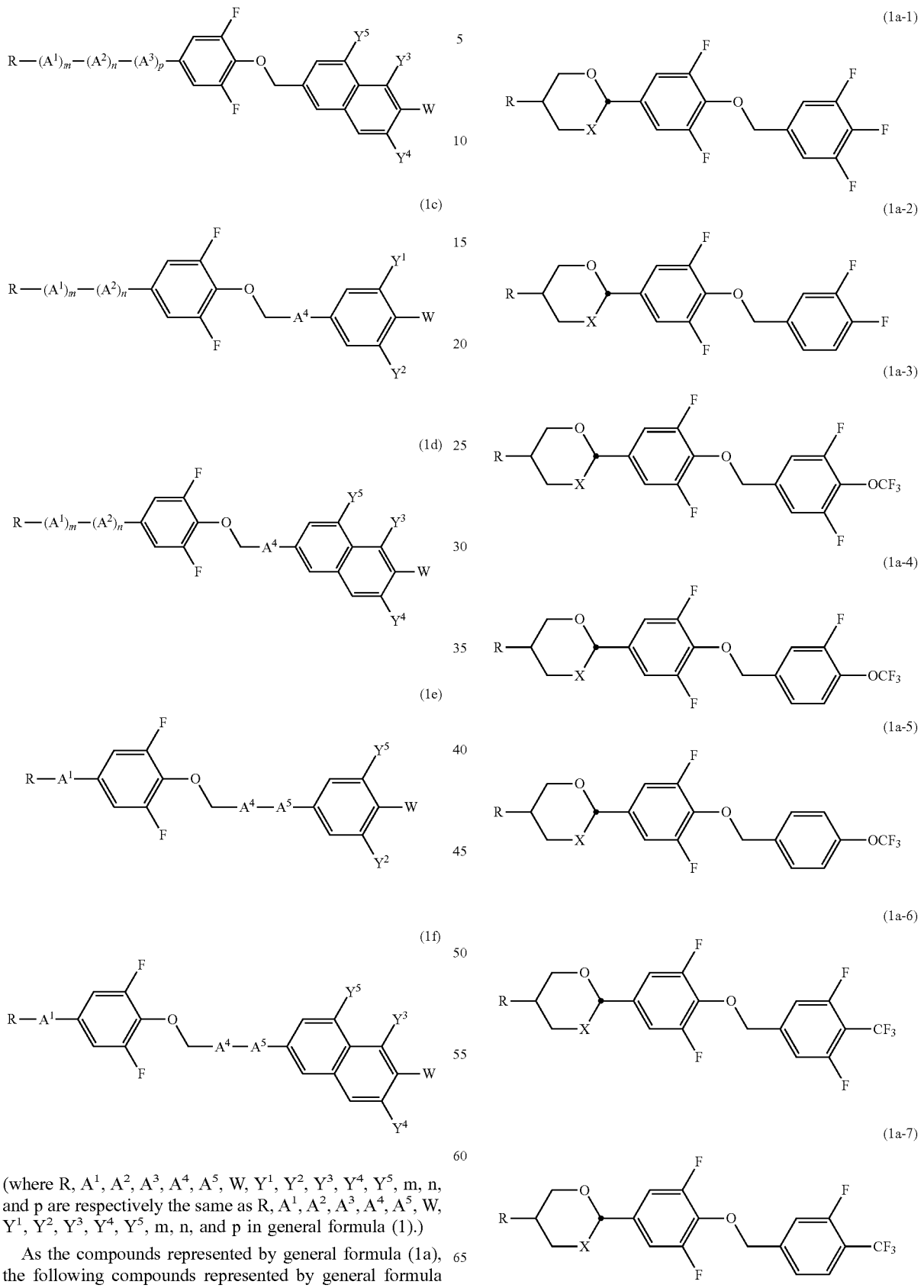
(where R, $A^1$, $A^2$, $A^3$, $A^4$, $A^5$, W, $Y^1$, $Y^2$, $Y^3$, $Y^4$, $Y^5$, m, n, and p are respectively the same as R, $A^1$, $A^2$, $A^3$, $A^4$, $A^5$, W, $Y^1$, $Y^2$, $Y^3$, $Y^4$, $Y^5$, m, n, and p in general formula (1).)
As the compounds represented by general formula (1a), the following compounds represented by general formula (1a-1) to general formula (1a-74) are more preferable.

(1a-8)
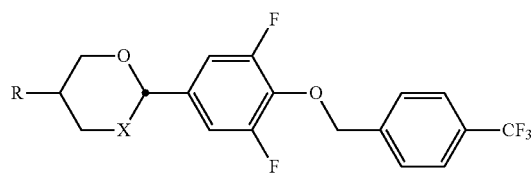
(1a-9)
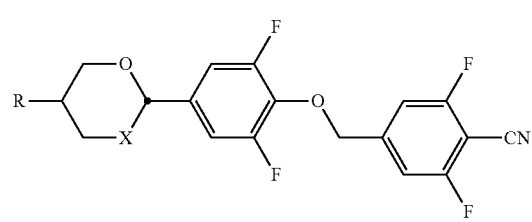
(1a-10)
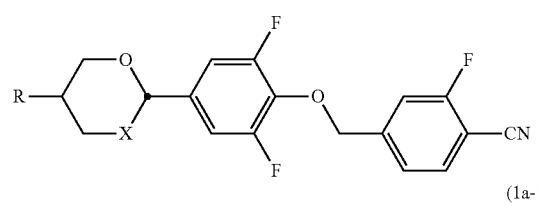
(1a-11)
(where R and X are the same as R and X in general formula (1), respectively.)
[Chem. 12]
(1a-12)
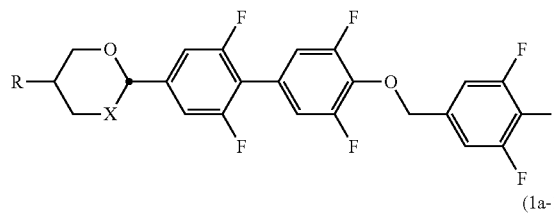
(1a-13)
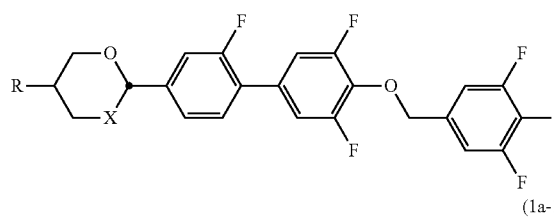
(1a-14)
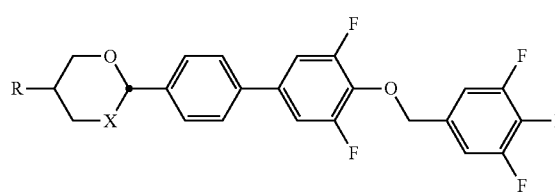
(1a-15)
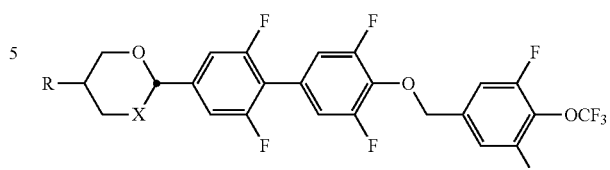
(1a-16)
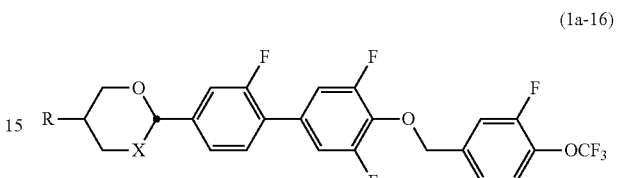
(1a-17)
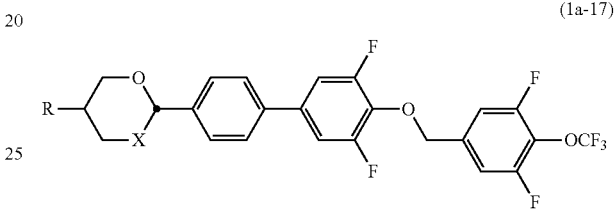
(1a-18)
(1a-19)
(1a-20)
(where R and X are the same as R and X in general formula (1), respectively.)
[Chem. 13]
(1a-21)
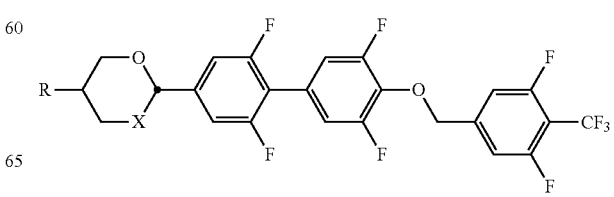

(where R and X are the same as R and X in general formula (1), respectively.)

[Chem. 14]

-continued
(1a-37)
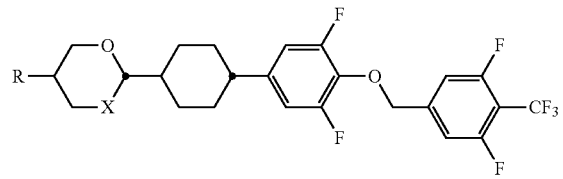
(1a-38)
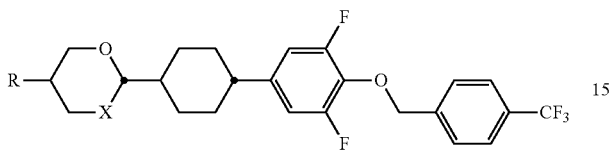
(1a-39)
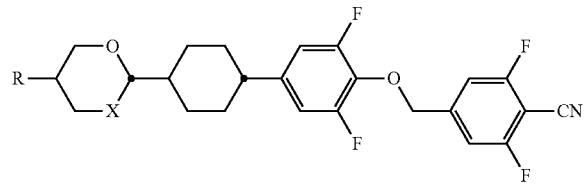
(1a-40)
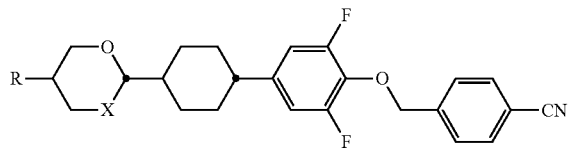
(where R and X are the same as R and X in general formula (1), respectively.)
[Chem. 15]
(1a-41)
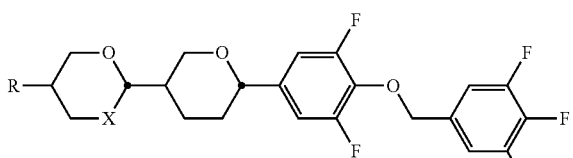
(1a-42)
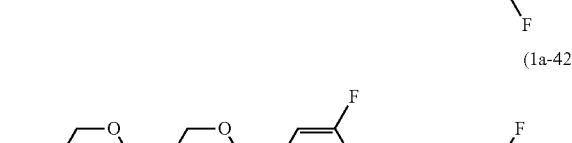
(1a-43)
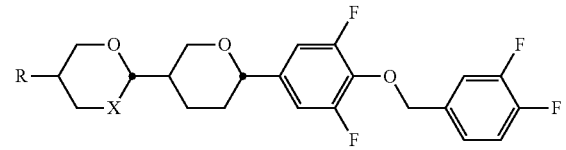
-continued
(1a-44)
(1a-45)
(1a-46)
(1a-47)
(1a-48)
(where R and X are the same as R and X in general formula (1), respectively.)
[Chem. 16]
(1a-49)
(1a-50)

(1a-51)
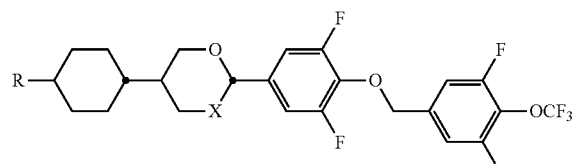
(1a-52)
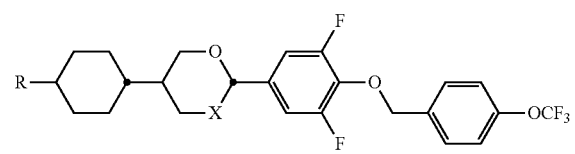
(1a-53)
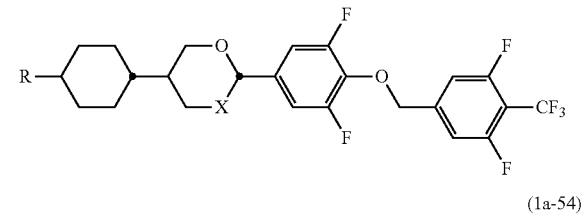
(1a-54)
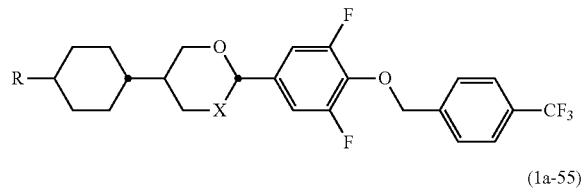
(1a-55)
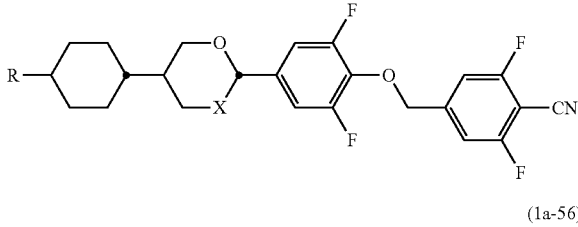
(1a-56)
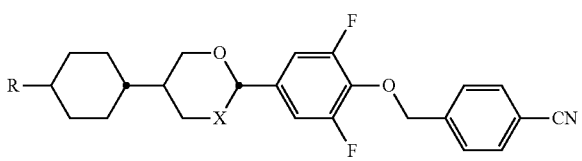
(where R and X are the same as R and X in general formula (1), respectively.)
[Chem. 17]
(1a-57)
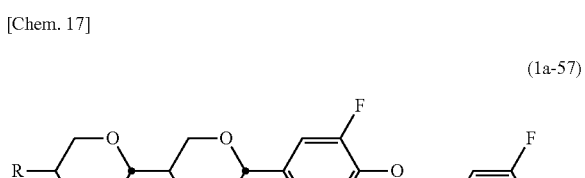
(1a-58)
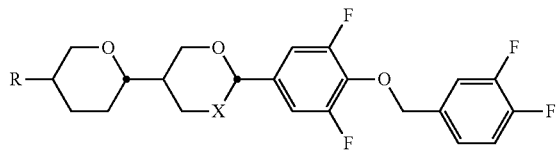
(1a-59)
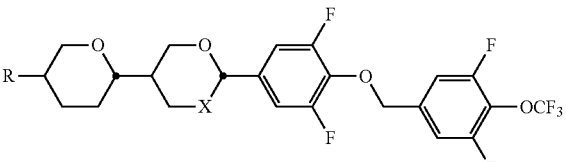
(1a-60)
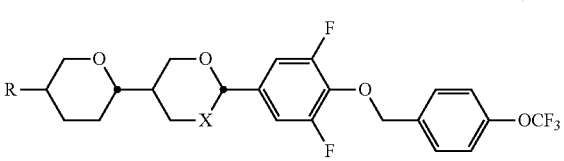
(1a-61)
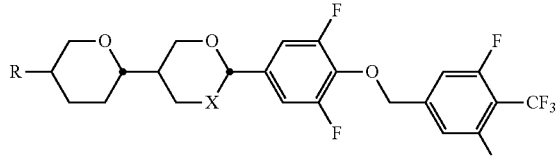
(1a-62)
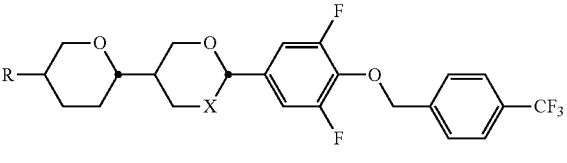
(1a-63)
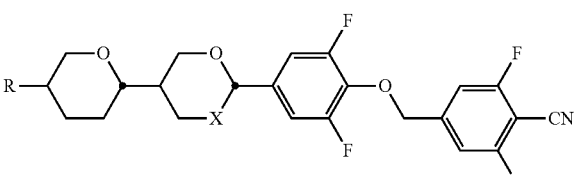
(1a-64)
(where R and X are the same as R and X in general formula (1), respectively.)

[Chem. 18]
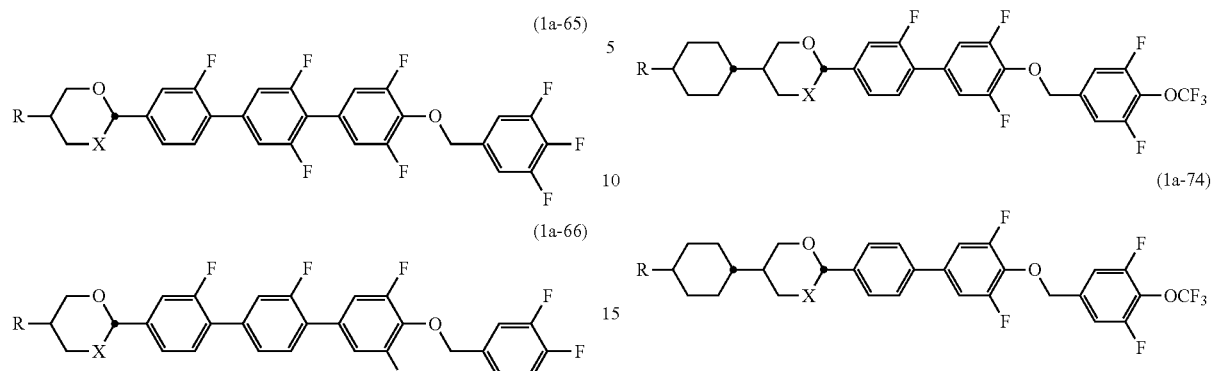
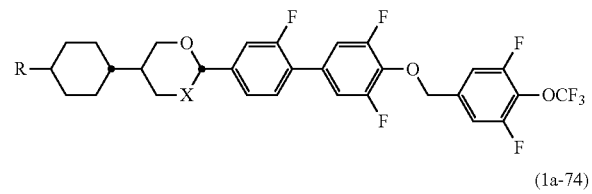
(where R and X are the same as R and X in general formula (1), respectively.)
As the compound represented by general formula (1b), compounds represented by general formula (1b-1) to general formula (1b-6) below are more preferable.
[Chem. 19]
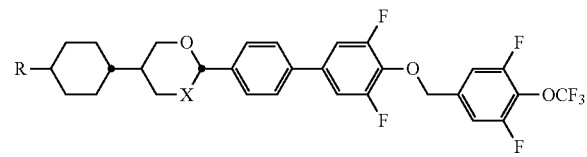
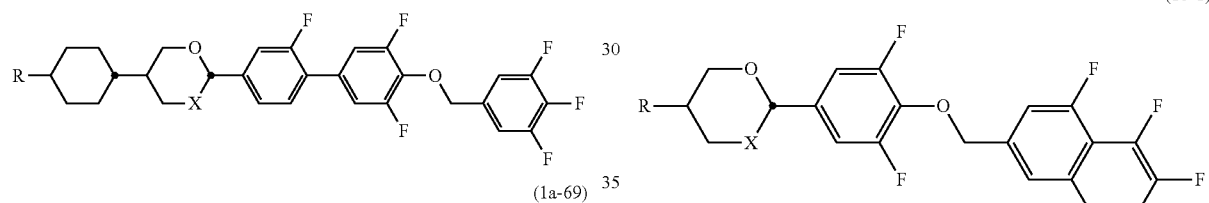

(1b-5)
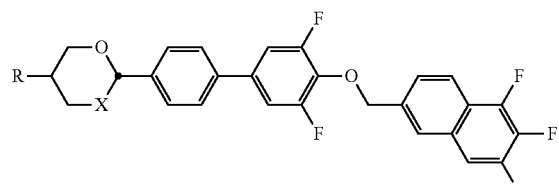
(1b-6)
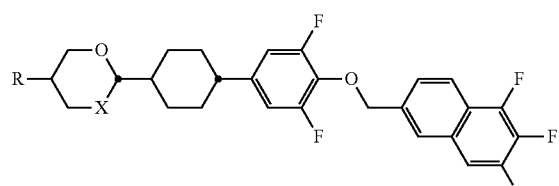
(where R and X are the same as R and X in general formula (1), respectively.)
As the compound represented by general formula (1c), compounds represented by general formula (1c-1) to general formula (1c-36) below are more preferable.
[Chem. 20]
(1c-1)
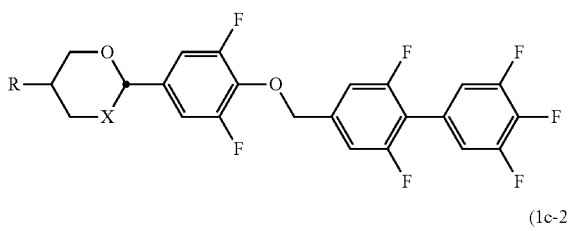
(1c-2)
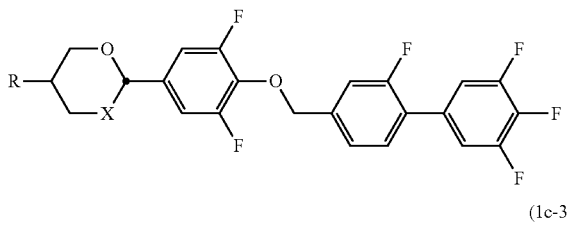
(1c-3)
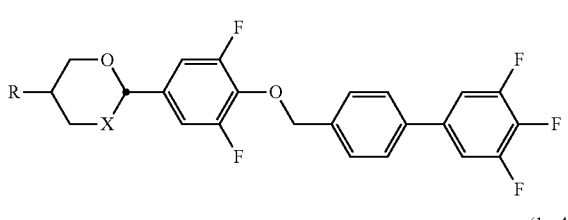
(1c-4)
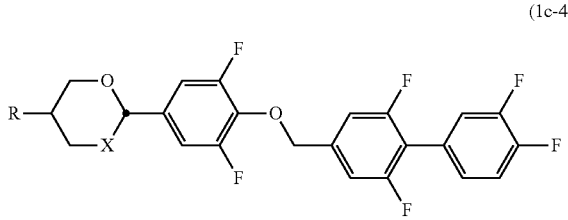
(1c-5)
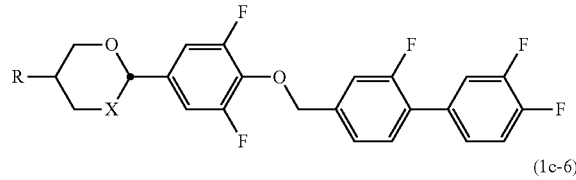
(1c-6)
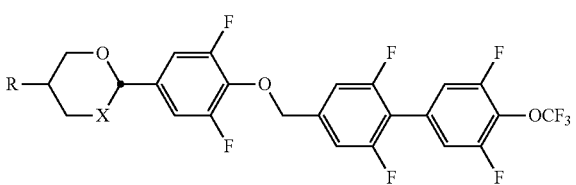
(1c-7)
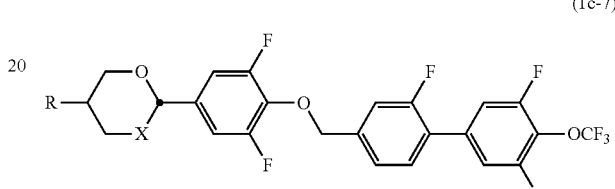
(1c-8)
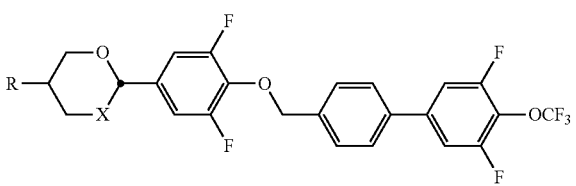
(1c-9)
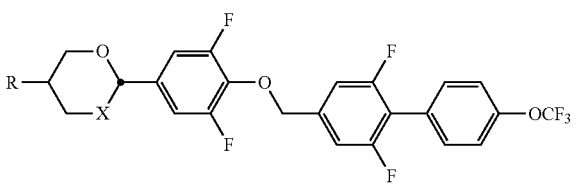
(1c-10)
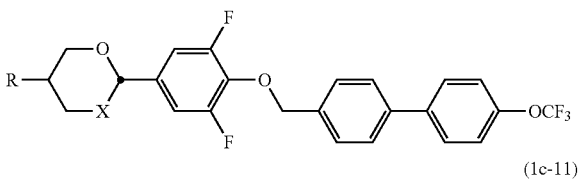
(1c-11)
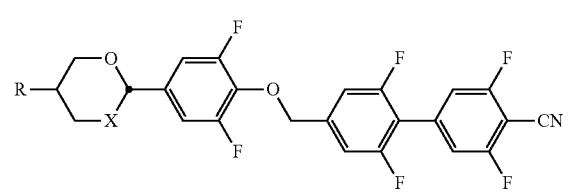
(1c-12)
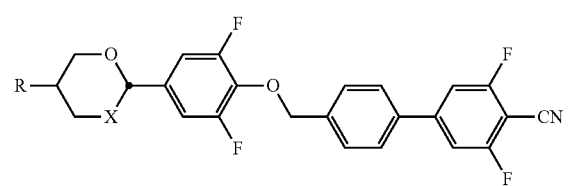

(where R and X are the same as R and X in general formula (1), respectively.)
[Chem. 21]
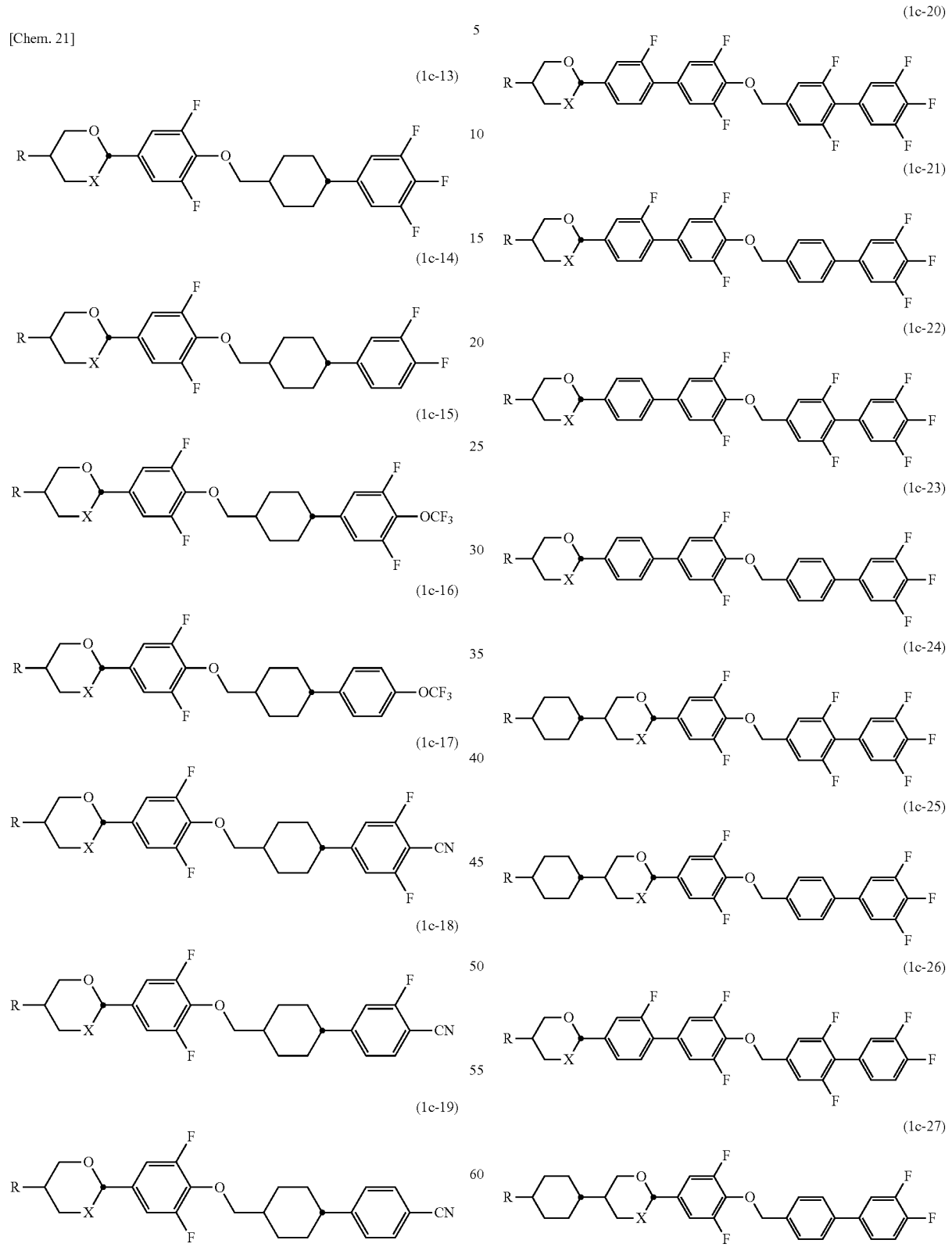
(where R and X are the same as R and X in general formula (1), respectively.)
[Chem. 22]
(where R and X are the same as R and X in general formula (1), respectively.)

[Chem. 23]
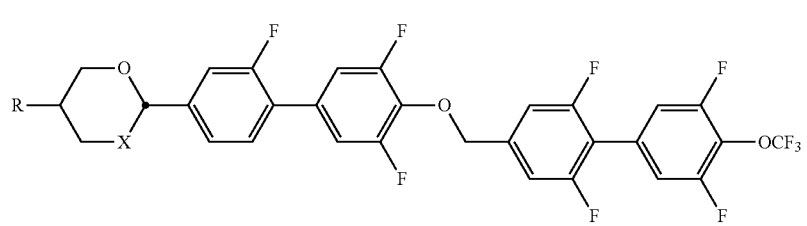
(1c-28)
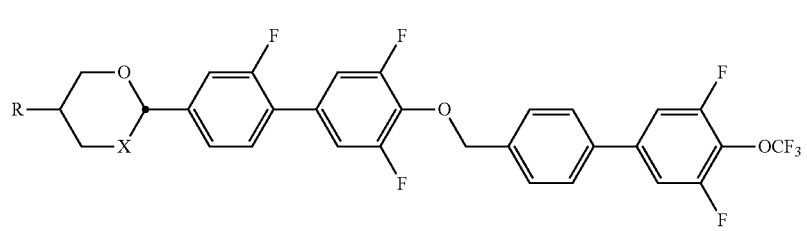
(1c-29)
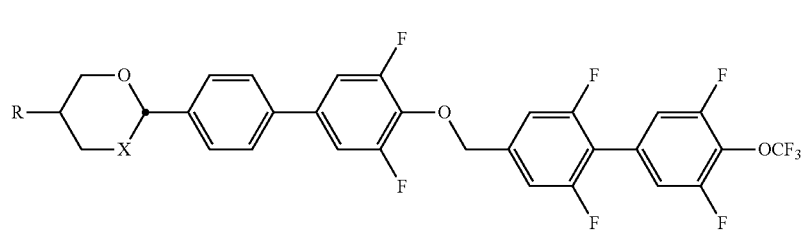
(1c-30)
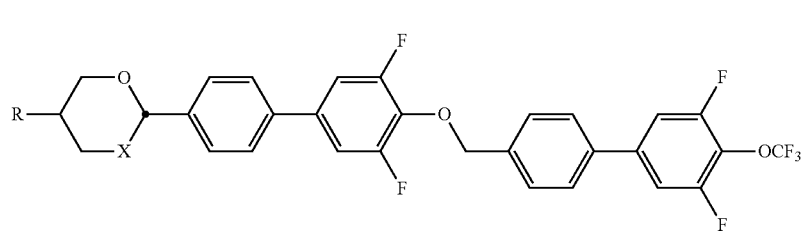
(1c-31)
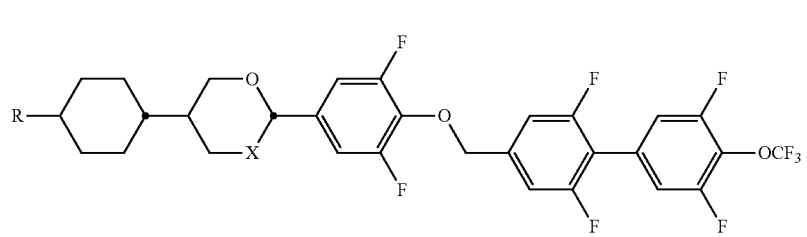
(1c-32)
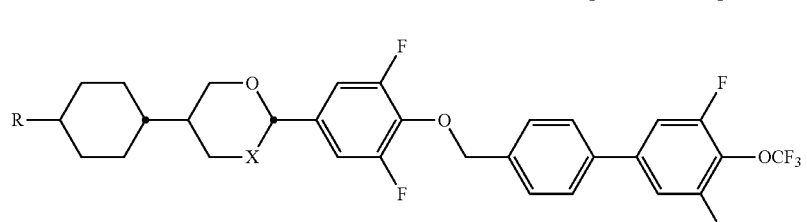
(1c-33)
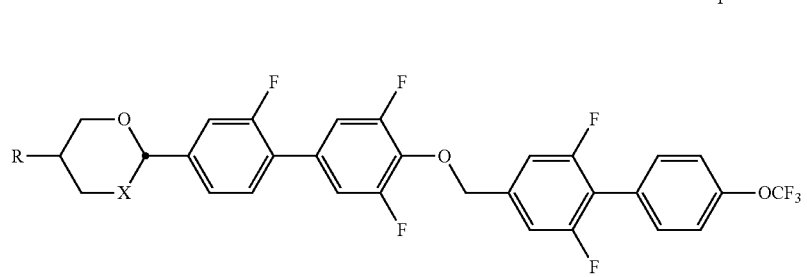
(1c-34)

(1c-35)
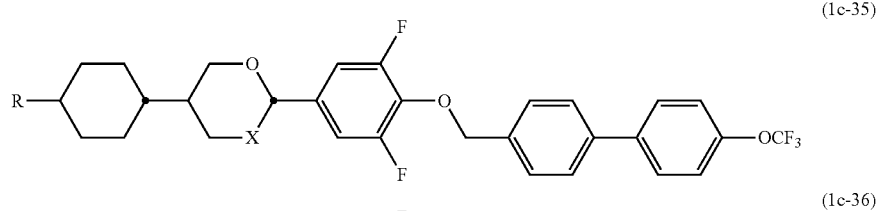
(1c-36)
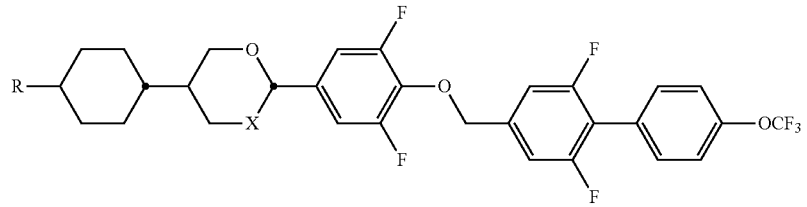
(where R and X are the same as R and X in general formula (1), respectively.)
As the compound represented by general formula (1d), compounds represented by general formula (1d-1) to general formula (1d-8) are more preferable.
[Chem. 24]
(1d-1)
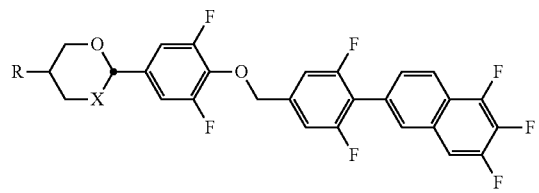
(1d-2)
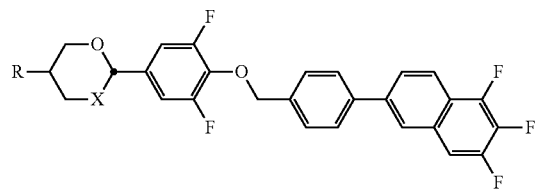
(1d-3)
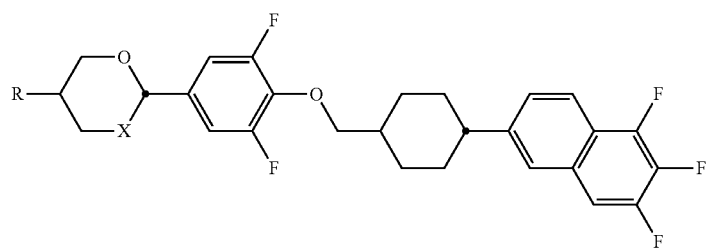
(1d-4)
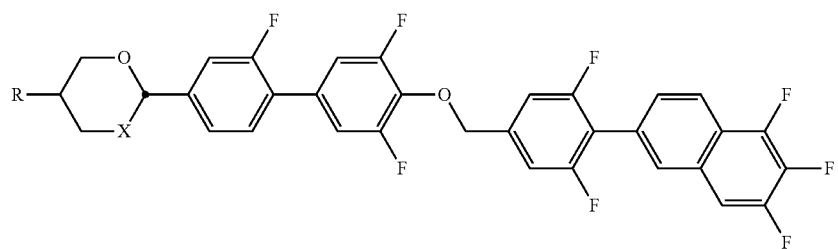
(1d-5)
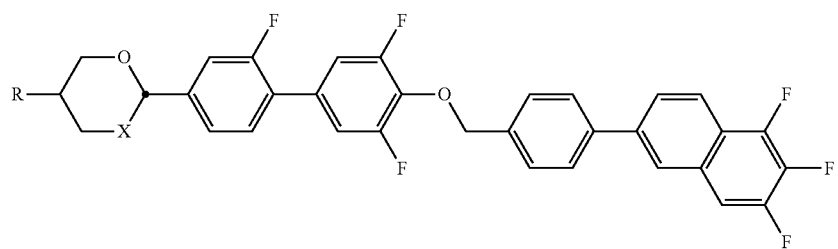

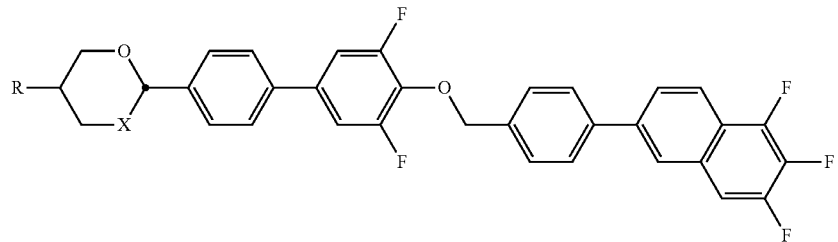
(1d-6)
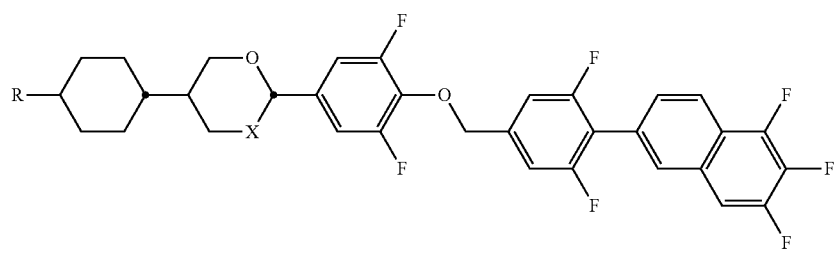
(1d-7)
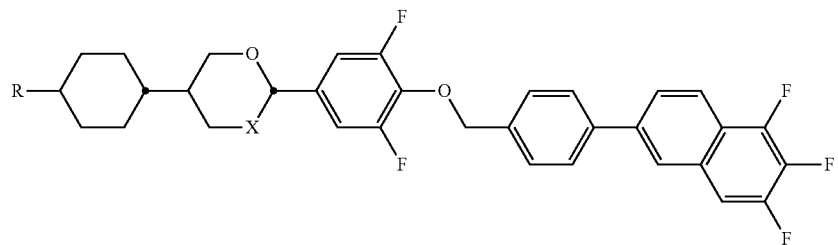
(1d-8)
(where R and X are the same as R and X in general formula (1), respectively.)
As the compound represented by general formula (1e), compounds represented by general formula (1e-1) to general formula (1e-20) below are more preferable.
[Chem. 25]
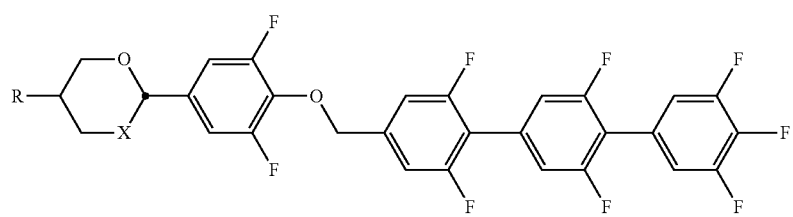
(1e-1)
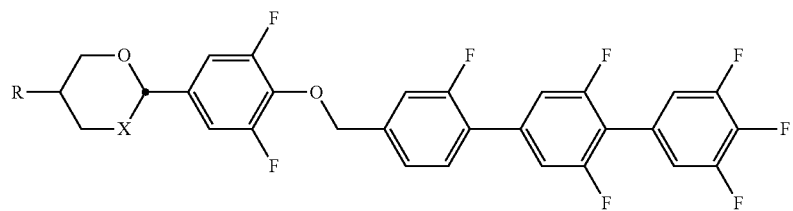
(1e-2)

-continued
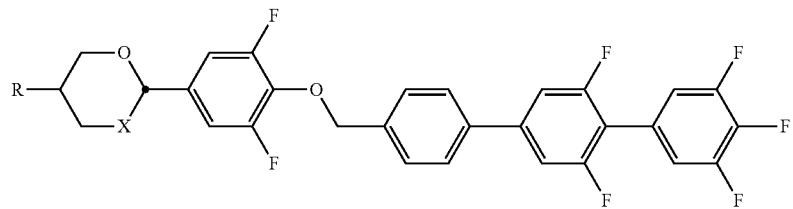
(1e-3)
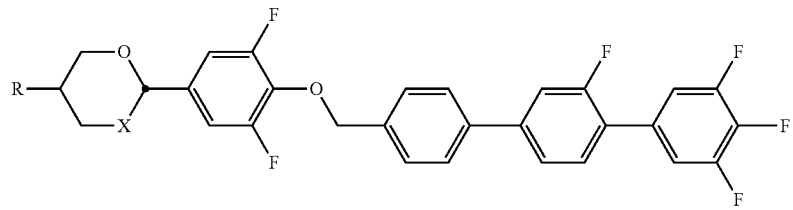
(1e-4)
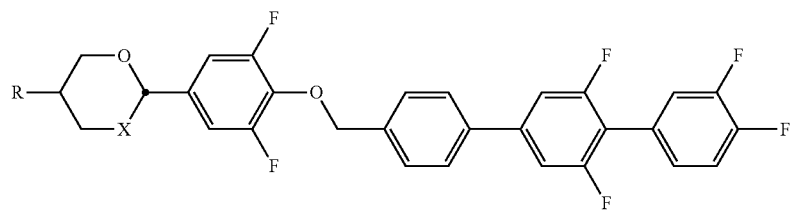
(1e-5)
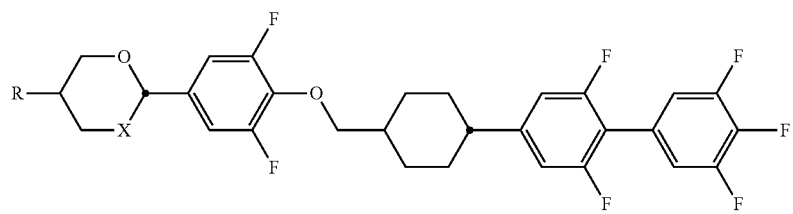
(1e-6)
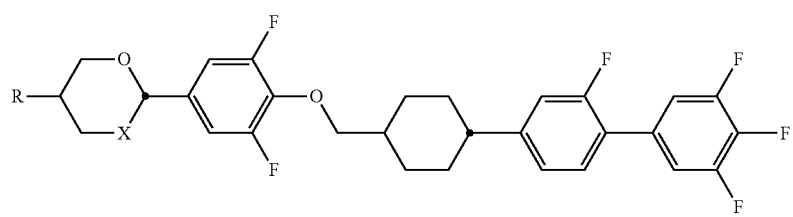
(1e-7)
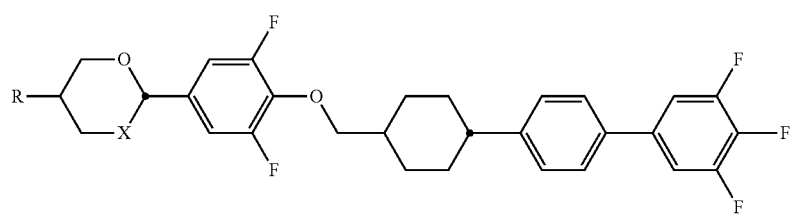
(1e-8)
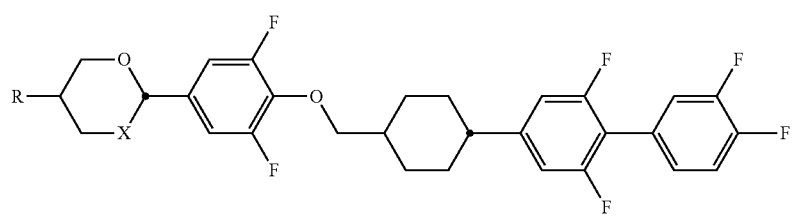
(1e-9)

-continued
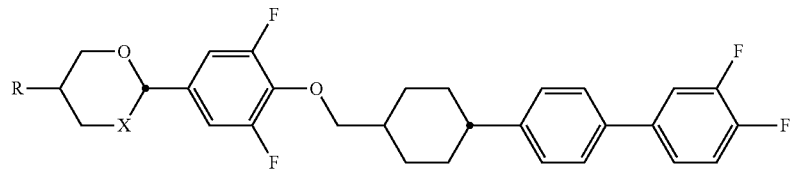
(1e-10)
(where R and X are the same as R and X in general formula 1), respectively.)
[Chem. 26]
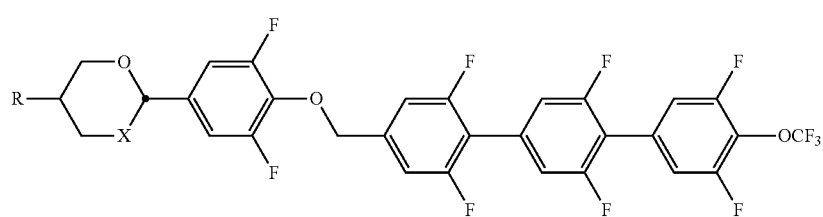
(1e-11)
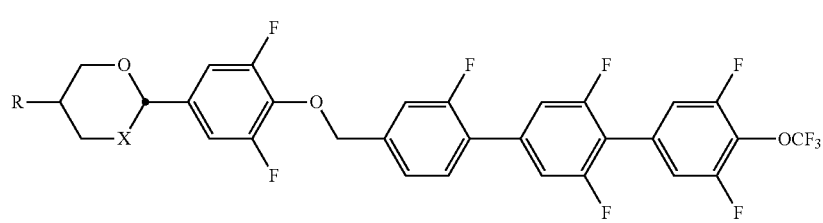
(1e-12)
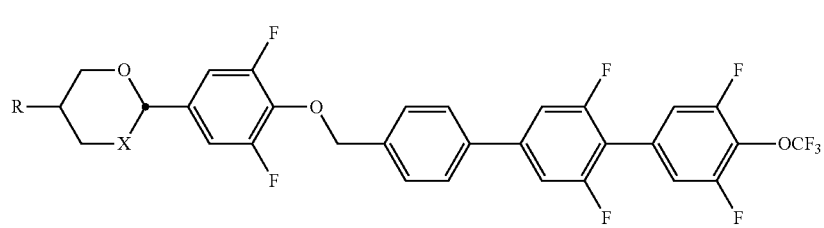
(1e-13)
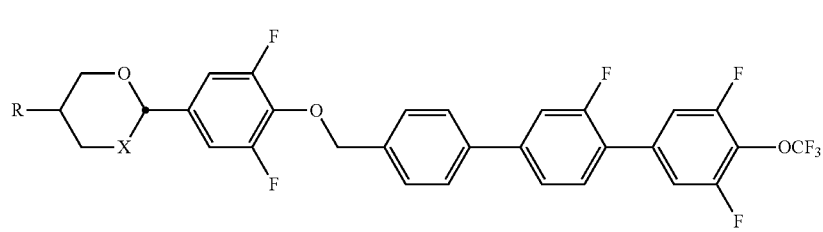
(1e-14)
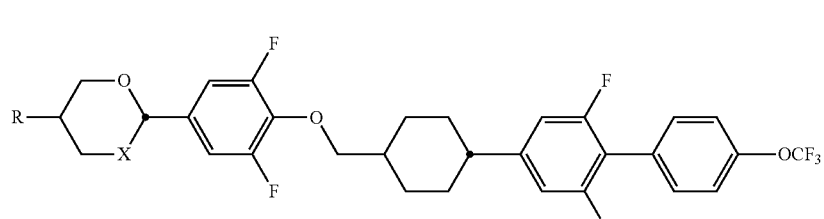
(1e-15)

(1e-16)
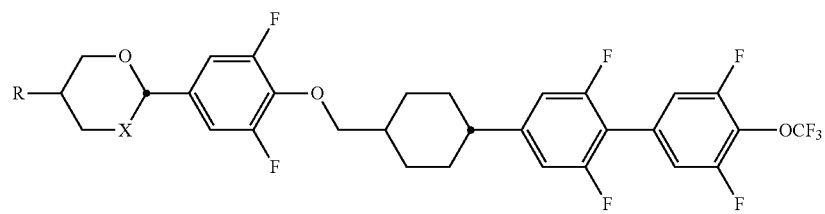
(1e-17)
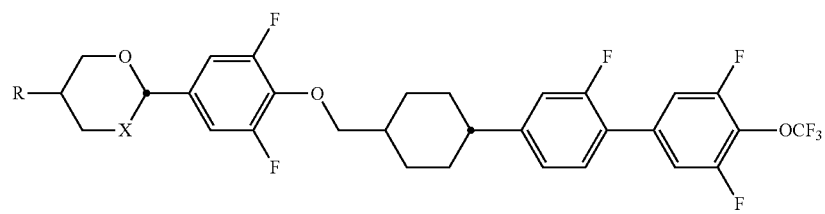
(1e-18)
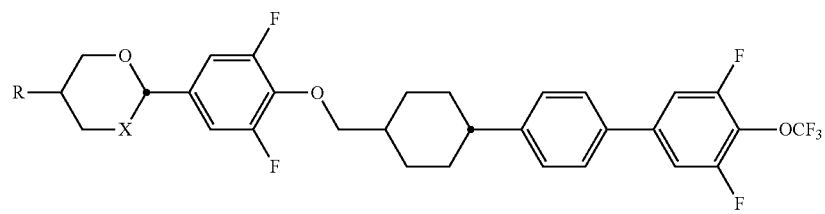
(1e-19)
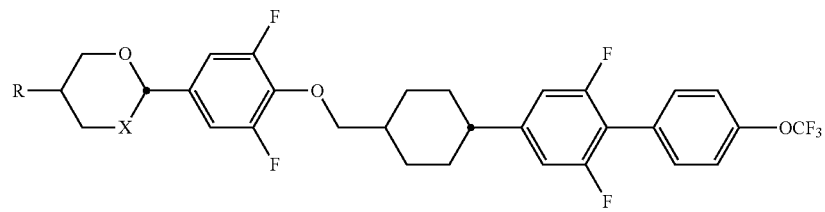
(1e-20)
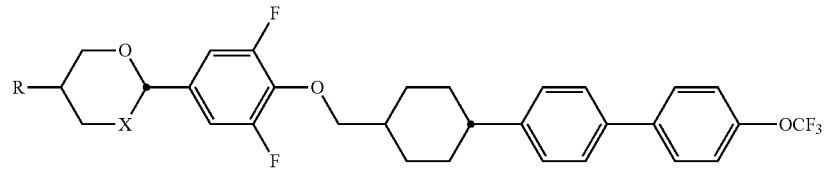
(where R and X are the same as R and X in general formula (1), respectively.)
As the compound represented by general formula (1f), compounds represented by general formula (1f-1) to general formula (1f-7) are more preferable.
[Chem. 27]
(1f-1)
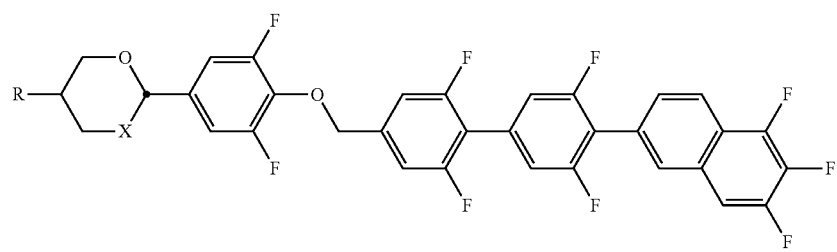

-continued

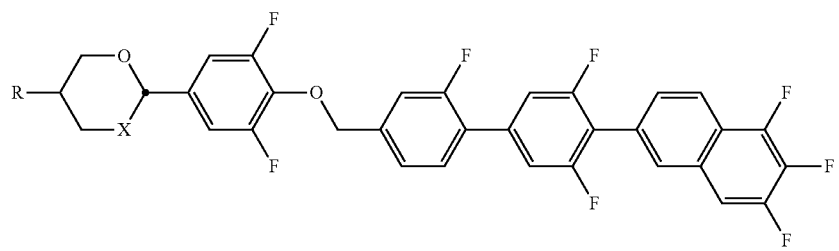
(1f-2)

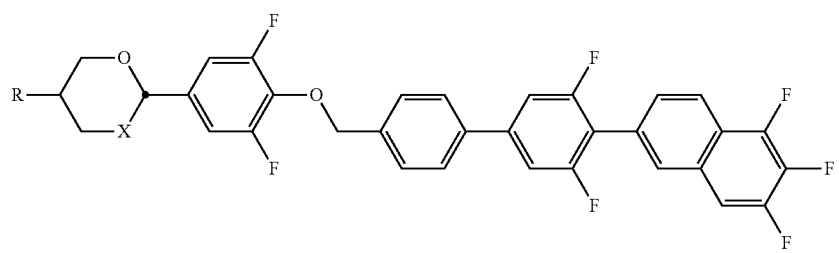
(1f-3)

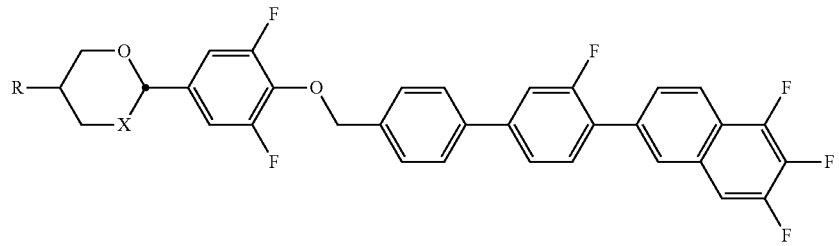
(1f-4)

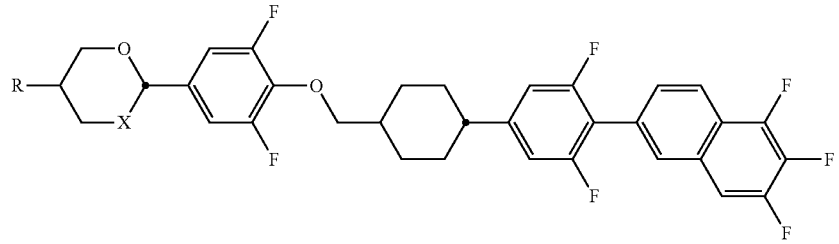
(1f-5)

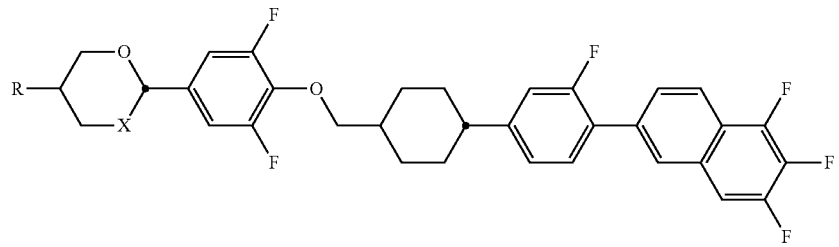
(1f-6)

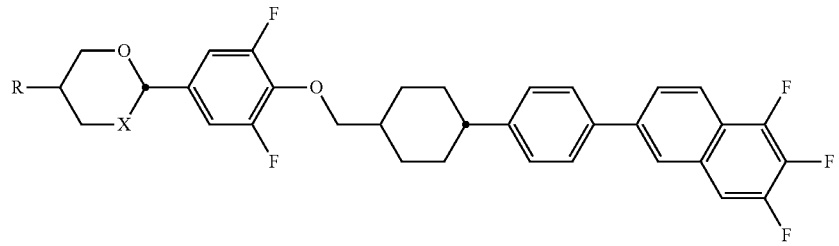
(1f-7)

(where R and X are the same as R and X in general formula (1), respectively.)

If the compound represented by general formula (1) is contained in a small amount in the liquid crystal composition of the present invention, the effect of the compound is not exhibited; thus, the lower limit of the amount of the compound represented by general formula (1) is 1% by mass (hereinafter % indicating the content represents % by mass)

or more, preferably 2% or more, and most preferably 5% or more. Since an excessively large content causes issues such as precipitation, the upper limit is preferably 50% or less, more preferably 30% or less, yet more preferably 20% or less, and most preferably 10% or less. The compounds represented by general formula (1) can be used alone or in combination or two or more.

In order to adjust physical property values of the liquid crystal composition, compounds other than those represented by general formula (1) may be used, and a compound that does not have a liquid crystal phase may be added in addition to compounds having a liquid crystal phase, if needed.

Preferable representative examples of compounds that can be used and mixed with compounds represented by general formula (1) are as follows. While the composition according to the present invention contains a least one compound represented by general formula (1) as a first component, at least one selected from second to fourth components described below is preferably contained as other components.

That is, a second component is a fluorine-based (halogen-based) p-type liquid crystal compound and examples thereof are compounds represented by general formulae (A1) to (A3) below:

[Chem. 28]

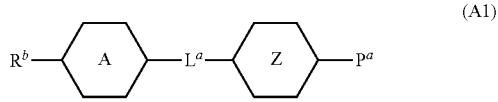
(A1)

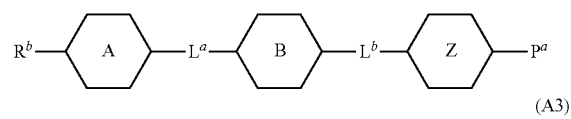
(A2)

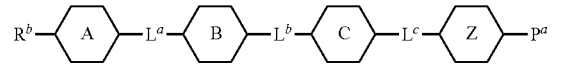
(A3)

In the above-described formulae, $R^b$ represents an alkyl group having 1 to 12 carbon atoms, the alkyl group may be linear or branched or may have a three- to six-membered ring structure, any —CH$_2$— in the group may be substituted with —O—, —CH=CH—, —CH=CF—, —CF=CH—, —CF=CF—, or —C≡C—, and any hydrogen atom in the group may be substituted with a fluorine atom or a trifluoromethoxy group. Preferably, $R^b$ represents a linear alkyl group having 1 to 7 carbon atoms, a linear 1-alkenyl group having 2 to 7 carbon atoms, a linear 3-alkenyl group having to 7 carbon atoms, or an alkyl group having 1 to 5 carbon atoms having a terminal substituted with an alkoxy group having 1 to 3 carbon atoms. When $R^b$ is branched and an asymmetric carbon occurs, the compound may be optically active or racemic.

Ring A, ring B, and ring C each independently represent a trans-1,4-cyclohexylene group (one CH$_2$ group or two or more non-adjacent CH$_2$ groups in the group may each be substituted with an oxygen atom), a transdecahydronaphthalene-trans-2,6-diyl group, a 1,4-phenylene group which may be substituted with one or more fluorine atoms (one CH group or two or more non-adjacent CH groups in the group may each be substituted with a nitrogen atom), a naphthalene-2,6-diyl group, a tetrahydronaphthalene-2,6-diyl group, a 1,4-cyclohexenylene group, a 1,3-dioxane-trans-2,5-diyl group, a pyrimidine-2,5-diyl group, or a pyridine-2,5-diyl group. One or more hydrogen atoms contained in these groups may each be substituted with F, Cl, CF$_3$, or OCF$_3$.

In particular, ring A, ring B, and ring C preferably each independently represent a trans-1,4-cyclohexylene group, a transdecahydronaphthalene-trans-2,6-diyl group, a naphthalene-2,6-diyl group which may be substituted with a fluorine atom, or a 1,4-phenylene group which may be substituted with one or two fluorine atoms. When ring B represents a trans-1,4-cyclohexylene group or a transdecahydronaphthalene-trans-2,6-diyl group, ring A preferably represents a trans-1,4-cyclohexylene group. When ring C represents a trans-1,4-cyclohexylene group or a transdecahydronaphthalene-trans-2,6-diyl group, ring B and ring A preferably each represent a trans-1,4-cyclohexylene group. In (A3), ring A preferably represents a trans-1,4-cyclohexylene group.

$L^a$, $L^b$, and $L^c$ are bonding groups and each independently represent a single bond, an ethylene group (—CH$_2$CH$_2$—), a 1,2-propylene group (—CH(CH$_3$)CH$_2$— and —CH$_2$CH(CH$_3$)—), a 1,4-butylene group, —COO—, —OCO—, —OCF$_2$—, —CF$_2$O—, —CH=CH—, —CH=CF—, —CF=CH—, —CF=CF—, —C≡C—, —OCH$_2$—, —CH$_2$O—, or —CH=NN=CH—, more preferably each independently represent a single bond, an ethylene group, a 1,4-butylene group, —COO—, —OCF$_2$—, —CF$_2$O—, —CF=CF—, or —C≡C—, and most preferably each independently represent a single bond or an ethylene group. In (A2), at least one of them preferably represents a single bond and in (A3), at least two of them preferably each represent a single bond.

Ring Z is an aromatic ring and represents any one of general formulae (La) to (Lc) below:

[Chem. 29]

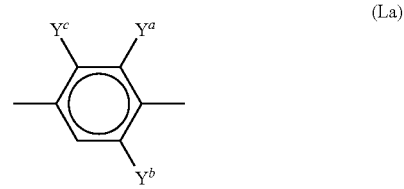
(La)

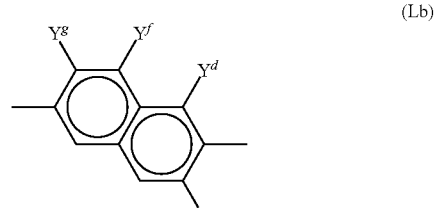
(Lb)

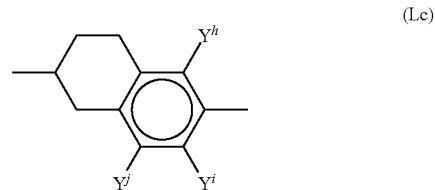
(Lc)

In the formulae, $Y^a$ to $Y^j$ each independently represent a hydrogen atom or a fluorine atom. In (La), at least one selected from $Y^a$ and $Y^b$ preferably represents a fluorine atom. In (Lb), at least one selected from $Y^d$ to $Y^f$ preferably represents a fluorine atom and $Y^d$ more preferably represents a fluorine atom. In (Lc), at least one selected from $Y^h$ and $Y^i$ preferably represents a fluorine atom and $Y^h$ more preferably represents a fluorine atom.

The terminal group $P^a$ represents a fluorine atom, a chlorine atom, a trifluoromethoxy group, a difluoromethoxy group, a trifluoromethyl group, a difluoromethyl group, a C2-C3 alkoxy group substituted with two or more fluorine atoms, C2-C3 alkyl group substituted with two or more fluorine atoms, C2-C3 alkenyl group substituted with two or more fluorine atoms, or a C2-C3 alkenyloxy group substituted with two or more fluorine atoms. The terminal group pa preferably represents a fluorine atom, a trifluoromethoxy group, or a difluoromethoxy group, and more preferably represents a fluorine atom.

The third component is a cyano-based p-type liquid crystal compound and examples thereof include compounds represented by general formulae (B1) to (B3) below.

[Chem. 30]

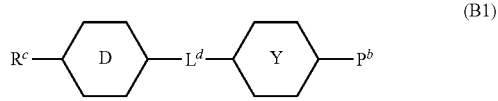

(B1)

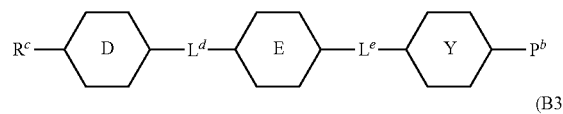

(B2)

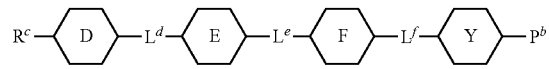

(B3)

In the formulae, $R^c$ represents an alkyl group having 1 to 12 carbon atoms, the alkyl group may be linear or branched or may have a three- to six-membered ring structure, any —$CH_2$— in the group may be substituted with —O—, —CH=CH—, —CH=CF—, —CF=CH—, —CF=CF—, or —C≡C—, and any hydrogen atom in the group may be substituted with a fluorine atom or a trifluoromethoxy group. Preferably, $R^c$ represents a linear alkyl group having 1 to 7 carbon atoms, a linear 1-alkenyl group having 2 to 7 carbon atoms, a linear 3-alkenyl group having 4 to 7 carbon atoms, or an alkyl group having 1 to 5 carbon atoms having a terminal substituted with an alkoxy group having 1 to 3 carbon atoms. When $R^c$ is branched and an asymmetric carbon occurs, the compound may be optically active or racemic.

Ring D, ring E, and ring F each independently represent a trans-1,4-cyclohexylene group (one $CH_2$ group or two or more non-adjacent $CH_2$ groups in the group may each be substituted with an oxygen atom), a transdecahydronaphthalene-trans-2,6-diyl group, a 1,4-phenylene group (one CH group or two or more non-adjacent CH groups in the group may each be substituted with a nitrogen atom), a naphthalene-2,6-diyl group, a tetrahydronaphthalene-2,6-diyl group, a 1,4-cyclohexenylene group, a 1,3-dioxane-trans-2,5-diyl group, a pyrimidine-2,5-diyl group, or a pyridine-2,5-diyl group. One or more hydrogen atoms contained in these groups may each be substituted with F, Cl, $CF_3$, or $OCF_3$.

In particular, ring D, ring E, and ring F preferably each independently represent a trans-1,4-cyclohexylene group, a transdecahydronaphthalene-trans-2,6-diyl group, a naphthalene-2,6-diyl group which may be substituted with a fluorine atom, or a 1,4-phenylene group which may be substituted with one or two fluorine atoms. When ring E represents a trans-1,4-cyclohexylene group or a transdecahydronaphthalene-trans-2,6-diyl group, ring D preferably represents a trans-1,4-cyclohexylene group. When ring F represents a trans-1,4-cyclohexylene group or a transdecahydronaphthalene-trans-2,6-diyl group, ring D and ring E preferably each represent a trans-1,4-cyclohexylene group. In (B3), ring D preferably represents a trans-1,4-cyclohexylene group.

$L^d$, $L^s$, and $L^f$ are bonding groups and each independently represent a single bond, an ethylene group (—$CH_2CH_2$—), a 1,2-propylene group (—$CH(CH_3)CH_2$— and —$CH_2CH(CH_3)$—), a 1,4-butylene group, —COO—, —OCO—, —$OCF_2$—, —$CF_2O$—, —CH=CH—, —CH=CF—, —CF=CH—, —CF=CF—, —C≡C—, —$OCH_2$—, —$CH_2O$—, or —CH=NN=CH—, more preferably each independently represent a single bond, an ethylene group, —COO—, —$OCF_2$—, —$CF_2O$—, —CF=CF—, or —C≡C—, and most preferably each independently represent a single bond, an ethylene group, or —COO—. In general formula (B2), at least one of them preferably represents a single bond and in general formula (B3), at least two of them each preferably represent a single bond.

$P^b$ represents a cyano group.

Ring Y is an aromatic ring and represents one of general formulae (Ld) to (Lf) below:

[Chem. 31]

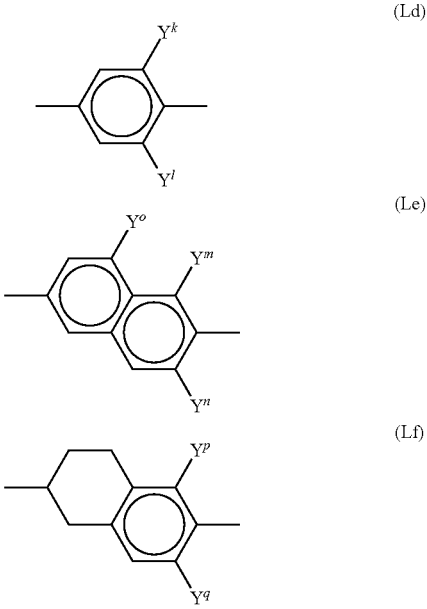

In the formulae, $Y^k$ to $Y^q$ each independently represent a hydrogen atom or a fluorine atom. In (Ld), at least one selected from $Y^k$ and $Y^l$ preferably represents a fluorine atom. In (Le), at least one selected from $Y^m$ to $Y^o$ preferably represents a fluorine atom and in particular $Y^m$ more preferably represents a fluorine atom. In (Lf), at least one selected from $Y^p$ and $Y^q$ preferably represents a fluorine atom and $Y^p$ more preferably represents a fluorine atom.

The fourth component is a non-polar liquid crystal compound having a dielectric anisotropy of about 0. Examples thereof include compounds represented by general formulae (C1) to (C3) below:

[Chem. 32]

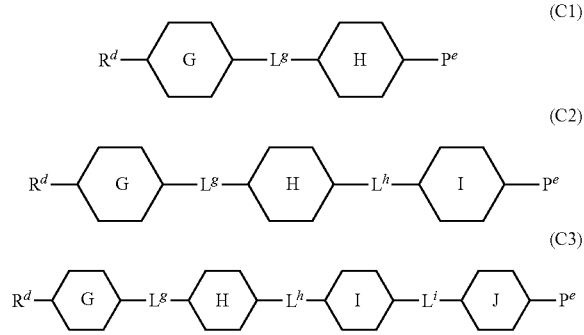

In the formulae, $R^d$ and $P^e$ each independently represent an alkyl group having 1 to 12 carbon atoms, the alkyl group may be linear or branched or may have a three- to six-membered ring structure, any —$CH_2$— in the group may be substituted with —O—, —CH=CH—, —CH=CF—, —CF=CH—, —CF=CF—, or —C≡C—, and any hydrogen atom in the group may be substituted with a fluorine atom or a trifluoromethoxy group. Preferably, $R^d$ and $P^e$ each independently represent a linear alkyl group having 1 to 7 carbon atoms, a linear 1-alkenyl group having 2 to 7 carbon atoms, a linear 3-alkenyl group having 4 to 7 carbon atoms, a linear alkoxy group having 1 to 3 carbon atoms, or a linear alkyl group having 1 to 5 carbon atoms having a terminal substituted with an alkoxy group having 1 to 3 carbon atoms. At least one selected from $R^d$ and $P^e$ more preferably represents a linear alkyl group having 1 to 7 carbon atoms, a linear 1-alkenyl group having 2 to 7 carbon atoms, or a linear 3-alkenyl group having 4 to 7 carbon atoms.

Ring G, ring H, ring I, and ring J each independently represent a trans-1,4-cyclohexylene group (one $CH_2$ group or two or more non-adjacent $CH_2$ groups in the group may each be substituted with an oxygen atom), a transdecahydronaphthalene-trans-2,6-diyl group, a 1,4-phenylene group which may be substituted with 1 or 2 fluorine atoms or methyl groups (one CH group or two or more non-adjacent CH groups in the group may each be substituted with a nitrogen atom), a naphthalene-2,6-diyl group which may be substituted with one or more fluorine atoms, a tetrahydronaphthalene-2,6-diyl group which may be substituted with 1 or 2 fluorine atoms, a 1,4-cyclohexenylene group which may be substituted with 1 or 2 fluorine atoms, a 1,3-dioxane-trans-2,5-diyl group, a pyrimidine-2,5-diyl group, or pyridine-2,5-diyl group. Each compound preferably contains up to one transdecahydronaphthalene-trans-2,6-diyl group, naphthalene-2,6-diyl group which may be substituted with one or more fluorine atoms, tetrahydronaphthalene-2,6-diyl group which may be substituted with 1 or 2 fluorine atoms, 1,4-cyclohexenylene group which may be substituted with one or two fluorine atoms, 1,3-dioxane-trans-2,5-diyl group, pyrimidine-2,5-diyl group, or pyridine-2,5-diyl group. Other rings are preferably each a trans-1,4-cyclohexylene group or a 1,4-phenylene group which may be substituted with one or two fluorine atoms or methyl groups. The total number of fluorine atoms present in ring G, ring H, ring I, and ring J is preferably 2 or less and more preferably 0 or 1.

$L^g$, $L^h$, and $L^i$ are bonding groups and each independently represent a single bond, an ethylene group (—$CH_2CH_2$—), a 1,2-propylene group (—CH($CH_3$)$CH_2$— and —$CH_2$CH($CH_3$)—), a 1,4-butylene group, —COO—, —OCO—, —OCF$_2$—, —CF$_2$O—, —CH=CH—, —CH=CF—, —CF=CH—, —CF=CF—, —C≡C—, or —CH=NN=CH—, and preferably each independently represent a single bond, an ethylene group, a 1,4-butylene group, —COO—, —OCO—, —OCF$_2$—, —CF$_2$O—, —CF=CF—, —C≡C—, —OCH$_2$—, —CH$_2$O—, or —CH=NN=CH—. In general formula (C2), at least one of them represents a single bond, and in general formula (C3), at least two of them each represent a single bond.

The compounds represented by general formulae (C1) to (C3) are other than the compounds represented by general formulae (A1) to (A3) and the compounds represented by general formulae (B1) to (B3).

In the compounds represented by general formulae (A1) to (A3), general formulae (B1) to (B3), and general formulae (C1) to (C3), hetero atoms will not directly bond to one another.

In the present invention, a compound represented by general formula (1) can be produced as follows. Naturally, the scope and application range of the present invention are not limited to these production examples.

(Production Method 1)

A compound represented by general formula (2)

[Chem. 33]

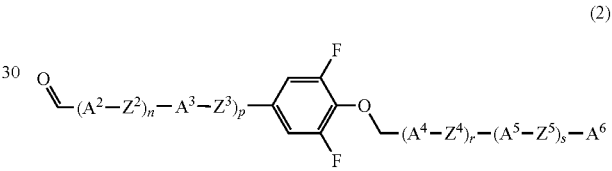

(where $A^2$, $A^3$, $A^4$, $A^5$, $A^6$, $Z^2$, $Z^3$, $Z^4$, and $Z^5$ are respectively the same as $A^2$, $A^3$, $A^4$, $A^5$, $A^6$, $Z^2$, $Z^3$, $Z^4$, and $Z^5$ in general formula (1), n, p, r, and s each independently represent 0 or 1, and n+p+r+s equals 0, 1, or 2) is subjected to dehydration condensation reaction in the presence of an acid catalyst to remove the compound represented by general formula (3)

[Chem. 34]

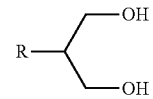

(where R is the same as R in general formula (1)) so that a compound represented by general formula (1) with $A^1$ representing a 1,3-dioxane-2,5-diyl group and $Z^1$ representing a single bond can be obtained.

The solvent used may be any solvent that can carry out smooth reaction. Examples thereof include aromatic solvents such as toluene, benzene, and xylene, ether solvents such as tetrahydrofuran (THF), diethyl ether, and diisopropyl ether, and halogen solvents such as dichloromethane, chloroform, and carbon tetrachloride. Benzene, toluene, and dichloromethane are preferable. These solvents can be used as a mixture if needed.

The reaction temperature may be any temperature at which reaction can be smoothly carried out. The reaction temperature is preferably room temperature or higher but not higher than the temperature at which the reaction solvent is refluxed. If the solvent used is azeotropic with water, water generated by the reaction under refluxing is more preferably separated and removed by using a Dean-Stark apparatus or the like.

The acid catalyst used may be any acid catalyst that can carry out smooth reaction. Preferable examples thereof include p-toluenesulfonic acid, chlorotrimethylsilane, and sulfuric acid. Sulfuric acid and p-toluenesulfonic acid are particularly preferable.

(Production Method 2)

A compound represented by general formula (2) is reacted with a compound represented by general formula (4) in the presence of an acid catalyst

[Chem. 35]

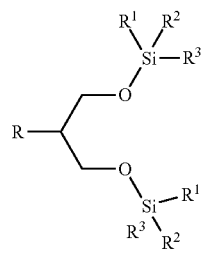

(4)

(where $R^1$, $R^2$, and $R^3$ each independently represent a hydrogen atom or an alkyl group having 1 to 5 carbon atoms which may be branched, and R is the same as R in general formula (1)) so that a compound represented by general formula (1) with $A^1$ representing a 1,3-dioxane-2,5-diyl group and $Z^1$ representing a single bond can be obtained.

The solvent used may be any solvent that can carry out smooth reaction. Examples thereof include halogen solvents such as dichloromethane, chloroform, and carbon tetrachloride, aromatic solvents such as benzene, toluene, and xylene, and ether solvents such as THF, diethyl ether, and diisopropyl ether. Dichloromethane and chloroform are more preferable. These solvents may be used as a mixture if needed.

The reaction temperature may be any temperature at which reaction can be smoothly carried out. The reaction temperature is preferably −78° C. to room temperature and more preferably −78° C. to −40° C.

Preferable examples of the acid catalyst used include trimethylsilyl trifluoromethanesulfonate and a boron trifluoride-diethyl ether complex. Trimethylsilyl trifluoromethanesulfonate is more preferable.

(Production Method 3)

A compound represented by general formula (5)

[Chem. 36]

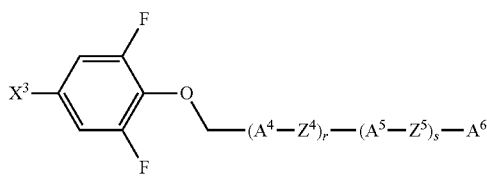

(5)

(where $X^3$ represents a chlorine atom, a bromine atom, or an iodine atom, $A^4$, $A^5$, $A^6$, $Z^4$, $Z^5$, r, and s are respectively the same as $A^4$, $A^5$, $A^6$, $Z^4$, $Z^5$, r, and s in general formula (1)) is reacted with a metallic magnesium, and then reacted with DMF so that a compound represented by general formula (6)

[Chem. 37]

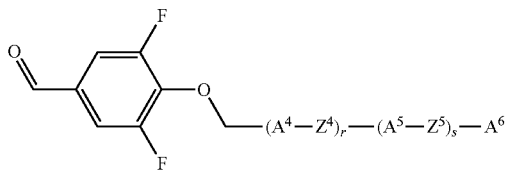

(6)

(where $A^4$, $A^5$, $A^4$, $Z^4$, $Z^5$, r, and s are respectively the same as $A^4$, $A^5$, $A^6$, $Z^4$, $Z^5$, r, and s in general formula (1)) can be obtained.

The solvent used may be any solvent that can carry out smooth reaction. Ether solvents such as THF, diethyl ether, and diisopropyl ether are preferable.

The reaction temperature may be any temperature at which reaction can be smoothly carried out. In reacting the compound represented by general formula (5) with metallic magnesium, the temperature is preferably 0° C. or higher but not higher than the temperature at which the solvent is refluxed. and is more preferably 20° C. or higher but not higher than the temperature at which the solvent is refluxed. In the subsequent reaction with DMF, the temperature is preferably −20° C. or higher but not higher than 20° C. and more preferably 0° C. to 10° C.

The subsequent steps are carried out by the method described in Production method (1) or (2). As a result, a compound represented by general formula (1) with $A^3$ representing a 1,3-dioxane-2,5-diyl group and $Z^3$ representing a single bond can be obtained.

(Production Method 4)

The compound represented by general formula (5) is reacted with an organic metal reagent and then with DMF so that a compound represented by general formula (6) can be obtained.

Examples of the organic metal reagent used include alkyl Grignard reagents such as methyl magnesium chloride, ethyl magnesium bromide, ethyl magnesium chloride, isopropyl magnesium chloride, and isopropyl magnesium bromide, and alkyl lithium reagents such as butyl lithium, sec-butyl lithium, and tert-butyl lithium. Isopropyl magnesium chloride, isopropyl magnesium bromide, butyl lithium, and sec-butyl lithium are more preferable. If needed, the organic metal reagent may be a complex with an inorganic salt such as lithium chloride.

The reaction temperature may be any temperature at which the reaction can be smoothly carried out. When an alkyl Grignard reagent is used as the organic metal reagent, the temperature is preferably −20° C. or higher but not higher than the temperature at which the solvent is refluxed and more preferably 0° C. to 20° C. When an alkyl lithium reagent is used as the organic metal reagent, the temperature is preferably −78° C. to 0° C. and more preferably −78° C. to −40° C.

The solvent used may be any solvent that can carry out smooth reaction. Examples thereof include ether solvents such as THF, diethyl ether, and diisopropyl ether and hydrocarbon solvents such as hexane and heptane. The solvent is more preferably THF.

The subsequent steps are carried out by the method described in Production method (1) or (2). As a result, a compound represented by general formula (1) with $A^3$ representing a 1,3-dioxane-2,5-diyl group and $Z^3$ representing a single bond can be obtained.

(Production Method 5)

A compound represented by general formula (7)

[Chem. 38]

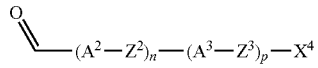
(7)

(where $A^2$, $A^3$, $Z^2$, and $Z^3$ are respectively the same as $A^2$, $A^3$, $Z^2$, and $Z^3$ in general formula (1), $X^4$ represents a chlorine atom, a bromine atom, or an iodine atom, and n and p each independently represent 0 or 1)
is subjected to dehydration condensation reaction in the presence of an acid catalyst so that the compound represented by general formula (3) is removed and a compound represented by general formula (8)

[Chem. 39]

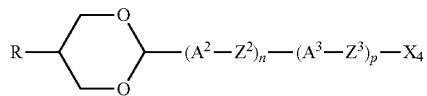
(8)

(where R, A2, A3, Z2, and Z3 are respectively the same as R, A2, A3, Z2, and Z3 in general formula (1), $X^4$ represents a chlorine atom, a bromine atom, or an iodine atom, and n and p each independently represent 0 or 1) can be obtained.

The solvent used may be any solvent that carry out smooth reaction. Examples thereof include aromatic solvents such as toluene, benzene, and xylene, ether solvents such as tetrahydrofuran (THF), diethyl ether, and diisopropyl ether, and halogen solvents such as dichloromethane, chloroform, and carbon tetrachloride. Benzene, toluene, and dichloromethane are preferable. These solvents may be used as a mixture, if needed.

The reaction temperature may be any temperature at which reaction can be smoothly carried out. The reaction temperature is preferably room temperature or higher but not higher than the temperature at which the reaction solvent is refluxed. If the solvent used is azeotropic with water, water generated by the reaction under refluxing is preferably separated and removed by using a Dean-Stark apparatus or the like.

The acid catalyst used may be any acid catalyst that can carry out smooth reaction. Preferable examples thereof include p-toluenesulfonic acid, chlorotrimethylsilane, and sulfuric acid. Sulfuric acid and p-toluenesulfonic acid are particularly preferable.

The compound represented by general formula (5) is sequentially reacted with an organic metal reagent and a borate ester, and then the resultant product is hydrolyzed so that a compound represented by general formula (9)

[Chem. 40]

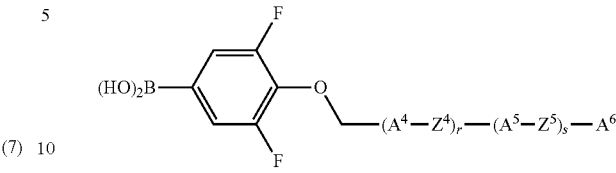
(9)

(where $A^4$, $A^5$, $A^6$, $Z^4$, $Z^5$, r, and s are respectively the same as $A^4$, $A^5$, $A^6$, $Z^4$, $Z^5$, r, and s in general formula (1)) can be obtained.

Examples of the organic metal reagent used include alkyl Grignard reagents such as methyl magnesium chloride, ethyl magnesium bromide, ethyl magnesium chloride, isopropyl magnesium chloride, and isopropyl magnesium bromide, and alkyl lithium reagents such as butyl lithium, sec-butyl lithium, and tert-butyl lithium. Isopropyl magnesium chloride, isopropyl magnesium bromide, butyl lithium, and sec-butyl lithium are more preferable. If needed, the organic metal reagent may be a complex with an inorganic salt such as lithium chloride.

The borate ester used may be any that can carry out smooth reaction but is preferably an alkyl borate ester such as trimethyl borate or triisopropyl borate. When an alkyl Grignard reagent is used as the organic metal reagent, trimethyl borate is more preferable. When an alkyl lithium reagent is used as the organic metal reagent, triisopropyl borate is more preferable.

The reaction temperature may be any temperature at which the reaction can be smoothly carried out. When an alkyl Grignard reagent is used as the organic metal reagent, the temperature is preferably −20° C. or higher but not higher than the temperature at which the solvent is refluxed and more preferably 0° C. to 20° C. When an alkyl lithium reagent is used as the organic metal reagent, the temperature is preferably −78° C. to 0° C. and more preferably −78° C. to −40° C.

The solvent used may be any solvent that can carry out smooth reaction. Examples thereof include ether solvents such as THF, diethyl ether, and diisopropyl ether and hydrocarbon solvents such as hexane and heptane. The solvent is more preferably THF.

Then a compound represented by general formula (8) is reacted with a compound represented by general formula (9) in the presence of a transition metal catalyst so that a compound represented by general formula (1) with $A^1$ representing a 1,3-dioxane-2,5-diyl group and $Z^1$ representing a single bond can be obtained.

The solvent used may be any solvent that can carry out smooth reaction. Examples thereof include ether solvents such as THF, diethyl ether, and diisopropyl ether, aromatic solvents such as benzene, toluene, and xylene, and amide solvents such as DMF, N,N-dimethylacetamide, and N-methylpyrrolidone. THF, DMF, and toluene are preferable. These solvents may be used alone or as a mixture if needed, and water may be added in order to smoothly carry out the reaction.

The reaction temperature may be any temperature at which reaction can be smoothly carried out. The reaction temperature is preferably room temperature or higher but not higher than the temperature at which the reaction solvent is refluxed, and is more preferably 40° C. or higher but not higher than the temperature at which the reaction solvent is refluxed.

The transition metal catalyst used may be any that can carry out smooth reaction. Preferable examples thereof include palladium-based transition metal catalysts and nickel-based transition metal catalysts such as tetrakis(triphenylphosphine)palladium(0), palladium(II) acetate, bis(triphenylphosphine)palladium(II) dichloride, [1,1'-bis(diphenylphosphino)ferrocene]palladium(II) dichloride, and bis[di-tert-butyl(4-dimethylaminophenyl)phosphine]palladium(II) dichloride. Tetrakis(triphenylphosphine)palladium(0), palladium(II) acetate, bis[di-tert-butyl(4-dimethylaminophenyl)phosphine]palladium(II) dichloride, and [1,1'-bis(diphenylphosphino)ferrocene]palladium(II) dichloride are more preferable. In order to accelerate progress of the reaction, a phosphine ligand may be added if needed.

(Production Method 6)

A compound represented by general formula (10)

[Chem. 41]

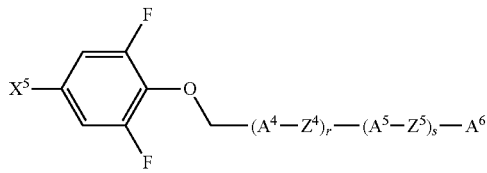

(10)

(where $X^5$ represents trifluoromethanesulfonyloxy group, a chlorine atom, a bromine atom, or an iodine atom, and $A^4$, $A^5$, $A^6$, $Z^4$, $Z^5$, r, and s are respectively the same as $A^4$, $A^5$, $A^6$, $Z^4$, $Z^5$, r, and s in general formula (1)) is reacted with a diborate cyclic diester in the presence of a transition metal catalyst so that a compound represented by general formula (11)

[Chem. 42]

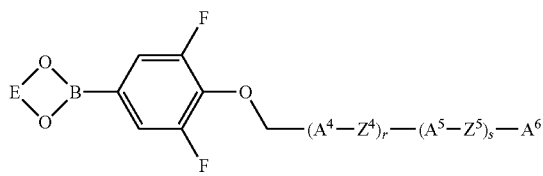

(11)

(where $A^4$, $A^5$, $A^6$, $Z^4$, $Z^5$, r, and s are respectively the same as $A^4$, $A^5$, $A^6$, $Z^4$, $Z^5$, r, and s in general formula (1), E represents —$(CH_2)_t$— in which one or more hydrogen atoms in the group may each independently be substituted with a methyl group, and t represents 2, 3, or 4) can be obtained.

The diborate cyclic diester used may be any that can carry out smooth reaction but is preferably bis(pinacolato)diboron.

The transition metal reagent used may be any that can carry out smooth reaction. Preferable examples thereof include palladium-based transition metal catalysts and nickel-based transition metal catalysts such as tetrakis(triphenylphosphine)palladium(0), palladium(II) acetate, bis(triphenylphosphine)palladium(II) dichloride, [1,1'-bis(diphenylphosphino)ferrocene]palladium(II) dichloride, and bis[di-tert-butyl(4-dimethylaminophenyl)phosphine]palladium(II) dichloride. Tetrakis(triphenylphosphine)palladium(0), palladium(II) acetate, bis[di-tert-butyl(4-dimethylaminophenyl)phosphine]palladium(II) dichloride, and [1,1'-bis(diphenylphosphino)ferrocene]palladium(II) dichloride are more preferable. In order to accelerate progress of the reaction, a phosphine ligand may be added if needed.

The solvent used may be any solvent that can carry out smooth reaction. Examples thereof include ether solvents such as THF, diethyl ether, and diisopropyl ether, aromatic solvents such as benzene, toluene, and xylene, amide solvents such as DMF, N,N-dimethylacetamide, and N-methylpyrrolidone, and dimethylsulfoxide. THF, DMF, toluene, and dimethylsulfoxide are more preferable. These solvents may be used alone or as a mixture if needed.

The reaction temperature may be any temperature at which reaction can be smoothly carried out. The reaction temperature is preferably room temperature or higher but not higher than the temperature at which the solvent is refluxed.

The subsequent steps are carried out by the method described in Production method (5). As a result, a compound represented by general formula (1) with $A^1$ representing a 1,3-dioxane-2,5-diyl group and $Z^1$ representing a single bond can be obtained.

(Production Method 7)

A compound represented by general formula (12)

[Chem. 43]

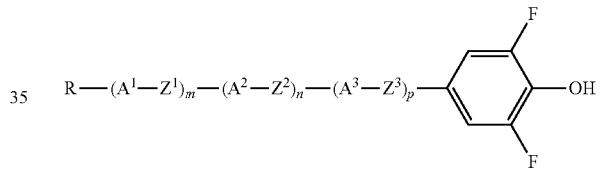

(12)

(where R, $A^1$, $A^2$, $A^3$, $Z^1$, $Z^2$, and $Z^3$ are respectively the same as R, $A^1$, $A^2$, $A^3$, $Z^1$, $Z^2$, and $Z^3$ in general formula (1), m, n, and p each independently represent 0 or 1, and at least one selected from m, n, and p represents 1)

is reacted with a compound represented by general formula (13)

[Chem. 44]

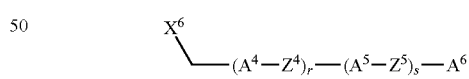

(13)

(where $X^6$ represents a hydroxyl group, a chlorine atom, a bromine atom, an iodine atom, a methanesulfonyloxy group, or a p-toluenesulfonyloxy group, $A^4$, $A^5$, $A^6$, $Z^4$, $Z^5$, r, and s are respectively the same as $A^4$, $A^5$, $A^6$, $Z^4$, $Z^5$, r, and s in general formula (1)) so that a compound represented by general formula (1) can be obtained.

When $X^6$ represents a hydroxyl group, the reaction is carried out in the presence of an azodicarboxylate ester such as diethyl azodicarboxylate or diisopropyl azodicarboxylate, or a phosphine such as triphenylphosphine.

The solvent used may be any solvent that can carry out smooth reaction. Preferable examples thereof include ether solvents such as THF, diethyl ether, and diisopropyl ether, halogen solvents such as dichloromethane, chloroform, and carbon tetrachloride, and hydrocarbon solvents such as hexane and toluene. THF is more preferable.

The reaction temperature may be any temperature at which the reaction can be smoothly carried out. The reaction temperature is preferably −30° C. to 40° C., more preferably −20° C. to 20° C., and most preferably −20° C. to ice-cool temperature.

When $X^6$ represents a chlorine atom, a bromine atom, a methanesulfonyloxy group, or a p-toluenesulfonyloxy group, the reaction is carried out in the presence of a base.

The reaction solvent used may be any solvent that can carry out smooth reaction. Preferable examples thereof include ether solvents such as THF, diethyl ether, and diisopropyl ether, amide solvents such as N,N-diformamide (DMF), N,N-dimethylacetamide, and N-methylpyrrolidone, and dimethyl sulfoxide. THF and DMF are more preferable. If needed, water may be added in addition to these solvents to conduct the reaction.

The reaction temperature may be any temperature at which the reaction can be smoothly carried out. The reaction temperature is preferably room temperature or higher but not higher than the temperature at which the solvent is refluxed, and more preferably 40° C. or higher but not higher than the temperature at which the solvent is refluxed.

The base used is preferably an alkali metal hydroxide such as sodium hydroxide or potassium hydroxide, or a carbonate salt such as sodium carbonate, potassium carbonate, or cesium carbonate. Potassium carbonate and cesium carbonate are more preferable.

A liquid crystal display device that uses a liquid crystal composition containing the compound of the present invention is useful since high-speed response and suppression of display failures are simultaneously achieved. In particular, the display device is useful as an active matrix driving liquid crystal display device, and can be applied to a liquid crystal display device of a VA mode, a PSVA mode, a PSA mode, an IPS mode, or an ECB mode.

Preferable embodiments of the liquid crystal display device according to the present invention will now be described in detail with reference to the drawings.

FIG. 1 is a cross-sectional view of a liquid crystal display device that includes two substrates opposing each other, a sealing member disposed between the substrates, and a liquid crystal enclosed in a sealed region surrounded by the sealing member.

Specifically, the liquid crystal display device includes a backplane, which is obtained by stacking a TFT layer 102 and a pixel electrode 103 on a substrate a 100 and then stacking a passivation film 104 and an alignment film a 105 thereon, and a frontplane obtained by stacking a black matrix 202, a color filter 203, a planarizing film (overcoat layer) 201, and a transparent electrode 204 on a substrate b 200 and then stacking an alignment film b 205 thereon. The backplane and the frontplane oppose each other. The liquid crystal display device further includes a sealing member 301 disposed between the substrates and a liquid crystal layer 303 enclosed in the sealed region surrounded by the sealing member. A projection 304 is formed on a substrate surface contacting the sealing member 301. Such a specific embodiment of the liquid crystal display device is shown in the drawing.

The substrate a and the substrate b may be composed of any material that is substantially transparent. Glass, ceramics, plastics, etc., can be used. For a plastic substrate, cellulose, cellulose derivatives such as triacetyl cellulose and diacetyl cellulose, polycycloolefin derivatives, polyesters such as polyethylene terephthalate and polyethylene naphthalate, polyolefins such as polypropylene and polyethylene, polycarbonate, polyvinyl alcohols, polyvinyl chloride, polyvinylidene chloride, polyamide, polyimide, polyimide amide, polystyrene, polyacrylate, polymethyl methacrylate, polyether sulfone, polyarylate, and inorganic-organic composite materials such as glass fiber-epoxy resin and glass fiber-acryl resin can be used.

In the case where a plastic substrate is used, a barrier film is preferably provided. The function of the barrier film is to decrease the moisture permeability of the plastic substrate and improve reliability of the electric properties of the liquid crystal display device. The barrier film is not particularly limited as long as the film has high transparency and low water vapor permeability. Typically, a thin film formed by using an inorganic material such as silicon oxide through vapor deposition, sputtering, or chemical vapor deposition (CVD) is used.

In the present invention, the same material or different materials may be used in the substrate a and the substrate b. Glass substrates are preferable since a liquid crystal display device having good heat resistance and dimensional stability can be fabricated. Plastic substrates are also preferable since they are suitable for a roll-to-roll production method, lightweight, and flexible. If flatness and heat resistance are desirable, a plastic substrate and a glass substrate are preferably used in combination since preferable results can be yielded.

In the backplane, the TFT layer 102 and the pixel electrode 103 are stacked on the substrate a 100. The TFT layer 102 and the pixel electrode 103 are produced through a typical array process. The passivation film 104 and the alignment film a 105 are stacked thereon and a backplane is obtained as a result.

The passivation film 104 (also referred to as an inorganic protective film) is a film that protects the TFT layer and is usually a nitride film (SiNx), an oxide film (SiOx), or the like by formed by chemical vapor deposition (CVD) technique or the like.

The alignment film a 105 has a function of aligning the liquid crystal and a polymer material such as polyimide is frequently used. An alignment agent solution formed of a polymer material and a solvent is used as the coating solution. The alignment film has a possibility of decreasing adhesive strength to the sealing member and is thus patterned and applied in the sealed region. A printing method such as flexo printing or a droplet ejection method such as ink jet is employed for application. After the solvent has evaporated by precuring, the applied alignment agent solution is crosslinked and cured by baking. Subsequently, an aligning process is performed to yield an aligning function.

The aligning process is usually performed by a rubbing technique. The polymer film formed as mentioned above is rubbed in one direction with a rubbing cloth composed of fibers such as rayon so as to yield a liquid crystal aligning ability.

Alternatively, an optical alignment technique is sometimes employed. The optical alignment technique is a technique of generating the aligning property by irradiation of an alignment film containing a photosensitive organic material with polarized light. According to this technique, scratching of the substrate and generation of dust that occur in the rubbing technique do not occur. Examples of the organic material used in the optical alignment technique include materials that contain dichroic dyes. Examples of the dichroic dyes that can be used include those which have groups (hereinafter simply referred to as optical alignment groups) that induce an optical reaction from which the liquid crystal alignment property originates, such as induction of molecular alignment or isomerization reaction (ex. azobenzene group) caused by Weigert's effect caused by dichroism, dimerization reaction (ex. cinnamoyl group), optical cross-linking reaction (ex. benzophenone group), or optical decomposition reaction (ex. polyimide group). The applied aligning agent solution is precured to evaporate the solvent and then irradiated with light (polarized light) having a desired polarization so as to obtain an alignment film having an aligning property in the desired direction.

The frontplane is constituted by the black matrix 202, the color filter 203, the planarizing film 201, the transparent electrode 204, and the alignment film b 205 stacked on the substrate b 200.

The black matrix 202 is, for example, produced by a pigment dispersion method. Specifically, a color resin solution containing an evenly dispersed black colorant for forming a black matrix is applied to the substrate b 200 having the barrier film 201 formed thereon so as to form a coloring layer. The coloring layer is then cured by baking. A photoresist is applied to the coloring layer and prebaked. The photoresist is exposed through a mask pattern and developed to perform patterning on the coloring layer. Then the photoresist layer is removed and the coloring layer is baked to form a black matrix 202.

Alternatively, a photoresist-type pigment dispersion may be used. In such a case, a photoresist-type pigment dispersion is applied, prebaked, exposed through a mask pattern, and developed to conduct patterning on the coloring layer. Then the photoresist layer is removed and the coloring layer is baked to form a black matrix 202.

The color filter 203 is prepared by a pigment dispersion method, an electrodeposition method, a printing method, or a dyeing method. For example, according to a pigment dispersion method, a color resin solution in which a pigment (for example, a red pigment) is evenly dispersed is applied to the substrate b 200 and cured by baking. Then a photoresist is applied thereto and prebaked. The photoresist is exposed through a mask pattern and then developed to perform patterning. The photoresist layer is then removed and baking is performed again. As a result, a (red) color filter 203 is obtained. The order of color in which the filters are made is not particularly limited. A green color filter 203 and a blue color filter 203 are made in the same manner.

The transparent electrode 204 is formed on the color filter 203 (if needed, an overcoat layer (201) for planarizing the surface may be formed on the color filter 203). The transmittance of the transparent electrode 204 is preferably high and the electrical resistance of the transparent electrode 204 is preferably low. The transparent electrode 204 is formed by sputtering or the like of an oxide film such as ITO.

A passivation film may be formed on the transparent electrode 204 to protect the transparent electrode 204.

The alignment film b 205 is the same as the alignment film a 105.

While specific embodiments of the backplane and the frontplane used in the present invention are described above, the subject application is not limited to these specific embodiments and these embodiments may be freely altered depending on the desired liquid crystal display device.

The shape of the columnar spacers is not particularly limited and its horizontal cross section may have a variety of shapes such as circular, rectangular, and other polygonal shapes. Considering the misalignment margin during the process, the horizontal cross section is particularly preferably circular or regular polygonal in shape. The shape of the projections is preferably a truncated cone or truncated pyramid.

The material of the columnar spacers is not particularly limited as long as it is a material that does not dissolve in the sealing member, the organic solvent used in the sealing member, or the liquid crystal. From the viewpoints of processing and weight reduction, a synthetic resin (curable resin) is preferable. The projections can be formed by a photolithographic method or a droplet ejection method on the surface of the first substrate that comes into contact with the sealing member. Due to these reasons, it is preferable to use a photocurable resin suitable for photolithography or a droplet ejection method.

The case in which the columnar spacers are obtained by a photolithographic method is described below as an example.

A resin solution for forming columnar spacers (not containing colorants) is applied to the transparent electrode 204 of the frontplane. Then this resin layer is cured by baking. A photoresist is applied thereto and prebaked. After exposing the photoresist through a mask pattern, development is conducted to conduct patterning of the resin layer. The photoresist layer is then removed and the resin layer is baked so as to complete formation of the columnar spacers.

The positions of forming the columnar spacers can be determined as desired by using a mask pattern. Accordingly, the columnar spacers can be formed inside the sealed region and outside the sealed region (portion where the sealing member is applied) of the liquid crystal display device simultaneously. The columnar spacers are preferably formed to be positioned on the black matrix so as not to degrade quality of the sealed region. The columnar spacers prepared by a photolithographic method as such are sometimes called column spacers or photo spacers.

A mixture containing a negative-type water-soluble resin such as PVA-stilbazo photosensitive resin, a polyfunctional acryl-based monomer, an acrylic acid copolymer, a triazole-based initiator, etc., is used as the material for the spacers. Alternatively, a color resin containing a colorant dispersed in a polyimide resin may be used. In the present invention, there are no limitation regarding spacers; spacers may be formed by using a known material while taking into account compatibility with the liquid crystal and the sealing member used.

After the columnar spacers are formed as such on the surface of the frontplane where a sealed region is to be formed, a sealing member (301 in FIG. 1) is applied to the surface that will make contact with the sealing member of the backplane.

The material for the sealing member is not particularly limited, and a curable resin composition containing a polymerization initiator and an epoxy-based or acryl-based photocurable, thermally curable, or photothermal dual curing resin is used. In order to control moisture permeability, elastic modulus, viscosity, etc., a filler composed of an inorganic material or an organic material is sometimes added. The shape of the filler is not particularly limited and may be spherical, fibrous, or irregular. A spherical gap material that has a monodisperse diameter or a fibrous gap material may be mixed in order to a satisfactorily control the cell gap; a fibrous substance that easily becomes entangled with the projections on the substrate may be added in order to further increase the adhesive strength to the substrate. The diameter of the fibrous substance used here is preferably about ⅕ to ⅒ of the cell gap or less. The length of the fibrous substance is preferably smaller than the width of the applied seal.

The material of the fibrous substance is not particularly limited as long as a desired shape can be obtained. A synthetic fiber such as cellulose, polyamide, or polyester, or an inorganic material such as glass or carbon can be appropriately selected.

A printing method and a dispensing method are available as the method for applying the sealing member. A dispensing method that uses less sealing member is preferable. The positions where the sealing member is applied are usually on a black matrix in order not to adversely affect the sealed region. In order to form a liquid crystal dropping region in the next step (in order to prevent leakage of the liquid crystals), the shape of the applied sealing member is a closed loop shape.

Liquid crystal is dropped within the closed loop (sealed region) of the frontplane to which the sealing member has been applied. Typically, a dispenser is used. The amount of liquid crystal to be dropped is basically equal to the volume obtained by multiplying the area of the applied seal and the height of the columnar spacer in order for the amount of the liquid crystal dropped to be equal to the cell volume. However, to deal with liquid crystal leakage that occurs in the cell bonding step and optimize display properties, the amount of the liquid crystal to be dropped may be appropriately adjusted or the positions where the liquid crystals are to be dropped may be scattered.

Next, the frontplane onto which the sealing member has been applied and the liquid crystals has been dropped is bonded to the backplane. Specifically, the frontplane and the backplane are held by respective stages having a substrate holding mechanism such as an electrostatic chuck and are arranged in such a manner that the alignment film b of the frontplane and the alignment film a of the backplane oppose each other and in such a position (distance) that the sealing member does not contact the other substrate. Under such conditions, the interior of the system is evacuated. Upon completion of evacuation, the positions of the two substrates are adjusted (alignment operation) while monitoring the position where the frontplane and the backplane are to be bonded to each other. After adjustment of the bonding position is finished, the substrates are brought to be close to each other up to a position where the sealing member on the frontplane contacts the backplane. Under these conditions, the interior of the system is filled with inert gas and the pressure is slowly returned to normal while releasing the evacuation. Due to this process, the frontplane and the backplane become bonded to each other due to atmospheric pressure, and a cell gap is formed at a height position of the columnar spacers. Under these conditions, the sealing member is irradiated with an ultraviolet ray to be cured and form a liquid crystal cell. Subsequently, a heating step is performed in some cases so as to accelerate curing of the sealing member. A heating step is frequently added so as to increase the adhesive strength of the sealing member and improve reliability of electrical properties.

Examples

The present invention will now be described in further detail by using Examples which do not limit the scope of the present invention.

The phase transition temperature was measured by using a polarizing microscope equipped with a temperature control stage, and a differential scanning calorimeter (DSC).

In Examples and Comparative Examples below, "%" associated with the content means "% by mass".

$T_{n-I}$ represents a nematic phase-isotropic phase transition temperature.

Following abbreviations are used to describe compounds:
THF: tetrahydrofuran
Me: methyl group, Pr: n-propyl group, Bu: n-butyl group Example 1

Production of trans-2-[4-(3,4,5-trifluorobenzyloxy)-3,5-difluorophenyl]-5-propyl-1,3-dioxane (1a-1)

[Chem. 45]

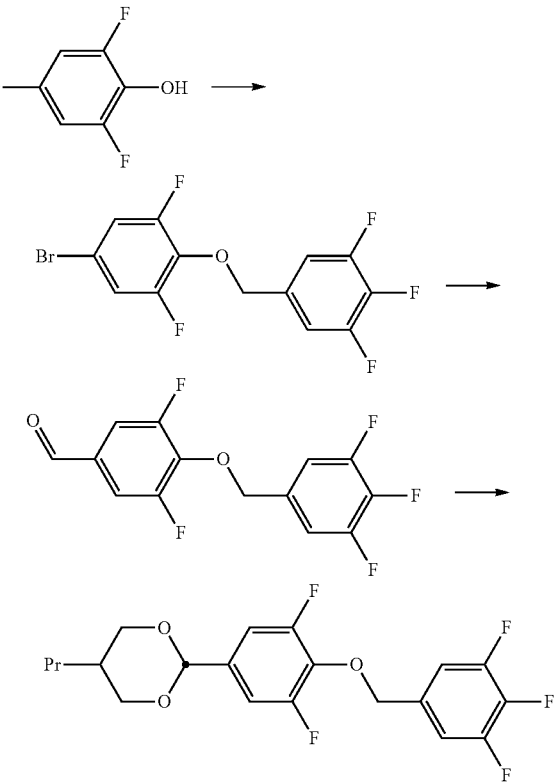

(1-1) In a nitrogen atmosphere, 4-bromo-2,6-difluorophenol (50 g), 3,4,5-trifluorobenzyl alcohol (38.8 g), and triphenylphosphine (69.0 g) were dissolved in THF (200 mL) and ice-cooled. Under cooling, diisopropyl azodicarboxylate (50.7 g) was slowly added thereto dropwise, and the resulting mixture was stirred at room temperature for 1 hour. After adding water (5 mL), the solvent was distilled away at a reduced pressure, the residue was suspended in hexane (400 mL), and insoluble matter was removed by filtration. The filtrate was concentrated at reduced pressure and purified through silica gel chromatography. As a result, crude 4-(3,4,5-trifluorobenzyloxy)-3,5-difluorobromobenzene (83.4 g) was obtained.

(1-2) In a nitrogen atmosphere, 4-(3,4,5-trifluorophenylmethyloxy)-3,5-difluorobromobenzene (83.4 g) obtained in (1-1) was dissolved in THF (400 mL) and ice-cooled. Under ice-cooling, a 14% isopropyl magnesium chloride-lithium chloride complex/THF solution (280 mL) was slowly added thereto dropwise, and the resulting mixture was stirred under ice-cooling for another hour. Under ice-cooling, a solution of DMF (25.9 g) dissolved in THF (100 mL) was slowly added thereto dropwise, and the resulting mixture was stirred at room temperature for 1 hour. Under ice-cooling, a 10% hydrochloric acid (300 mL) was slowly added thereto, and the resulting mixture was stirred at room temperature for 15 minutes and separated. Toluene (300 mL) was added to the aqueous layer to conduct extraction, and the organic layers were combined, washed twice with saturated saline (400 mL), and dried by addition of anhydrous sodium sulfate. The solvent was distilled away at a reduced pressure, the residue was purified by alumina column chromatography, and recrystallized from methanol. As a result, 4-(3,4,5-trifluorobenzyloxy)-3,5-difluorobenzaldehyde (61.1 g) was obtained.

(1-3) In a nitrogen atmosphere, 4-(3,4,5-trifluorobenzyloxy)-3,5-difluorobenzaldehyde (61.1 g) obtained in (1-2), 2-propyl-1,3-propanediol (23.8 g), and p-toluenesulfonic acid monohydrate (1.9 g) were suspended in toluene (300 mL), and the resulting suspension was stirred for 4 hours while removing generated water by using a Dean-Stark apparatus under solvent refluxing. After the resulting mixture was left to cool, a saturated aqueous sodium hydrogen carbonate solution (200 mL) was added to conduct separation. The organic layer was washed with saturated saline (200 mL) and dried by addition of anhydrous sodium sulfate. After distilling away the solvent at reduced pressure, the residue was purified by silica gel column chromatography and was recrystallized four times from a methanol-acetone mixed solvent. As a result, trans-2-[4-(3,4,5-trifluorobenzyloxy)-3,5-difluorophenyl]-5-propyl-1,3-dioxane (17.5 g) was obtained.

MS m/z: 402 [M+]

Phase transition temperature (° C.): Cr 40 Iso $^1$HNMR (CDCl$_3$, TMS internal standard) δ (ppm)=7.16 (2H, t, J=7.0 Hz), 6.70 (2H, d, J=8.8 Hz), 5.35 (1H, s), 5.10 (2H, s), 3.95-3.86 (4H, m), 2.65-2.46 (3H, m), 1.64-1.56 (2H, m), 0.92 (3H, t, J=7.2 Hz)

Example 2

Production of trans-2-[4-(4-(3,4,5-trifluorobenzyloxy)-3,5-difluorophenyl)-3-fluorophenyl]-5-propyl-1,3-dioxane (1a-12)

[Chem. 46]

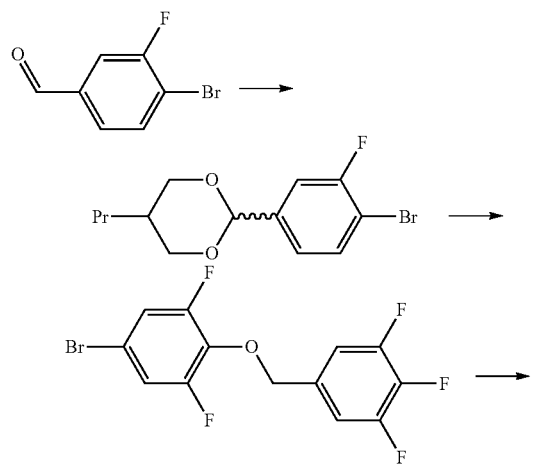

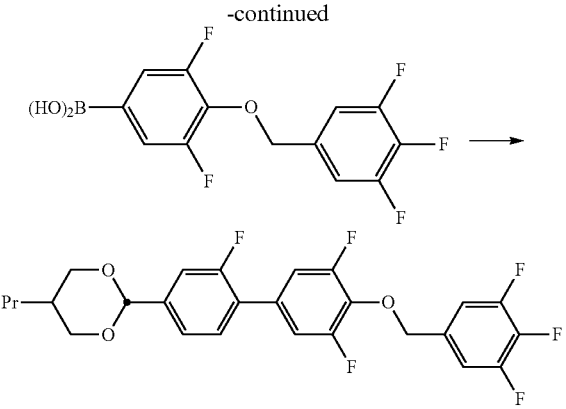

(2-1) In a nitrogen atmosphere, 4-bromo-3-fluorobenzaldehyde (20.0 g), 2-propyl-1,3-propanediol (11.6 g), and p-toluenesulfonic acid monohydrate (0.9 g) were dissolved in toluene (100 mL), and the resulting solution was stirred for four hours under solvent refluxing while removing generated water with a Dean-Stark apparatus. After the mixture was left to cool, a saturated aqueous sodium hydrogen carbonate solution (100 mL) was added thereto to conduct separation, and the organic layer was washed with saturated saline (100 mL) and dried by addition of anhydrous sodium sulfate. After the solvent was distilled away at a reduced pressure, the residue was purified by silica gel column chromatography. As a result, crude 2-(4-bromo-3-fluorophenyl)-5-propyl-1,3-dioxane (31.0 g) was obtained.

(2-2) In a nitrogen atmosphere, metallic magnesium (3.6 g) was suspended in THF (15 mL), and to the resulting suspension, a solution of 4-(3,4,5-trifluorophenylmethyloxy)-3,5-difluorobromobenzene (35.0 g) obtained in (1-1) dissolved in THF (100 mL) was added at such a rate that the inner temperature remained lower than 40° C. After stirring the resulting mixture for 1 hour at room temperature, a solution of trimethyl borate (15.4 g) dissolved in THF (30 mL) was slowly added thereto under ice-cooling. After stirring the resulting mixture for 2 hours at room temperature, a 10% hydrochloric acid (50 mL) was slowly added thereto to conduct separation. Toluene (100 mL) was added to the aqueous layer to conduct extraction, and the combined organic layers were washed with saturated saline (150 mL) and dried by addition of anhydrous sodium sulfate. The solvent was distilled away at reduced pressure. As a result, crude 4-(3,4,5-trifluorobenzyloxy)-3,5-difluorophenylboric acid (30.2 g) was obtained.

(2-3) In a nitrogen atmosphere, 2-(4-bromo-3-fluorophenyl)-5-propyl-1,3-dioxane (24.0 g) obtained in (2-1), tetrakis(triphenylphosphine)palladium(0) (3.7 g), a 2 mol % aqueous potassium hydrogen carbonate solution (80 mL), and THF (150 mL) were mixed and heated to 60° C. Under heating, a solution of 4-(3,4,5-trifluorobenzyloxy)-3,5-difluorophenylboric acid (30.2 g) obtained in (2-2) dissolved in THF (100 mL) was slowly added thereto dropwise, and the resulting mixture was stirred at 60° C. for 8 more hours. After the mixture was left to cool, water (100 mL) was added to conduct separation, toluene (100 mL) was added to the aqueous layer to conduct extraction, and the combined organic layers were washed with saturated saline (200 mL) and dried by addition of anhydrous sodium sulfate. After the solvent was distilled away, the residue was purified by silica gel chromatography and re-crystallized three times from an ethanol-acetone mixed solvent. As a result, trans-2-[4-(4-(3, 4,5-trifluorobenzyloxy)-3,5-difluorophenyl)-3-fluorophenyl]-5-propyl-1,3-dioxane (4.8 g) was obtained.

MS m/z: 496 [M+]

¹HNMR (CDCl₃, TMS internal standard) δ (ppm)=7.27 (1H, d, J=8.0 Hz), 7.15 (2H, t, J=7.1 Hz), 7.06-6.97 (2H, m), 6.70 (2H, d, J=8.8 Hz), 5.35 (1H, s), 5.11 (2H, s), 3.96-3.86 (4H, m), 2.65-2.48 (3H, m), 1.64-1.56 (2H, m), 0.92 (3H, t, J=7.1 Hz)

Example 3

Production of trans-2-[4-(4-(5,6,7-trifluoronaphthalen-2-yl)benzyloxy)-3,5-difluorophenyl]-5-propyl-1,3-dioxane (1d-2)

[Chem. 47]

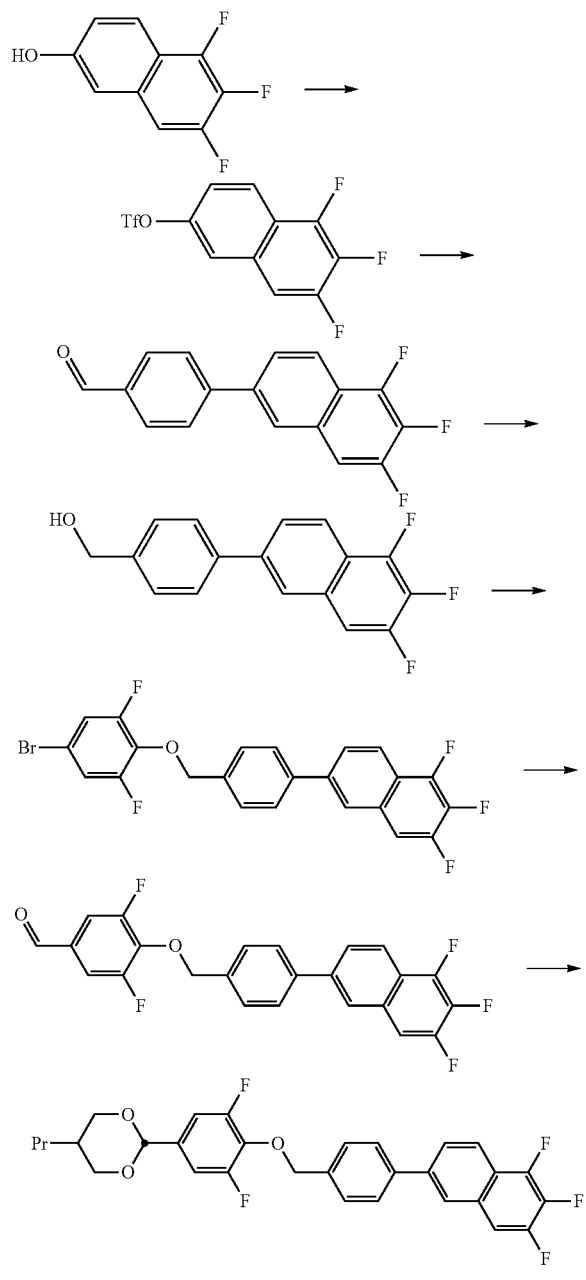

(3-1) In a nitrogen atmosphere, 5,6,7-trifluoro-2-naphthol (50 g, produced according to Japanese Unexamined Patent Application Publication No. 2004-91361) and pyridine (24.0 g) were dissolved in dichloromethane (250 mL) and the resulting solution was ice-cooled. Under ice-cooling, a solution of trifluoromethanesulfonic anhydride (78.5 g) dissolved in dichloromethane (150 mL) was slowly added thereto. After the mixture was stirred at room temperature for 3 hours, a 1 mol/L hydrochloric acid (200 mL) was added under ice-cooling to conduct separation. The organic layer was washed with water (200 mL), a saturated aqueous sodium hydrogen carbonate solution (200 mL), and saturated saline (200 mL), and dried by addition of anhydrous sodium sulfate. After the organic solvent was distilled away at reduced pressure, the residue was purified by silica gel chromatography. As a result, 5,6,7-trifluoro-naphthalen-2-yl trifluoromethanesulfonate (82.1 g) was obtained.

(3-2) In a nitrogen atmosphere, 5,6,7-trifluoro-naphthalen-2-yl trifluoromethanesulfonate (30.0 g) obtained in (3-1), tetrakis(triphenylphosphine)palladium(0) (5.6 g), a 2 mol % aqueous potassium hydrogen carbonate solution (120 mL), and THF (150 mL) were mixed and heated to 60° C. Under heating, a solution of 4-formylphenylboronic acid (20.0 g) dissolved in THF (60 mL) was added slowly thereto dropwise, and the resulting mixture was stirred for another hour at 60° C. After the mixture was left to cool to room temperature, water (120 mL) was added to conduct separation, toluene (150 mL) was added to the aqueous layer to conduct extraction, and the combined organic layers were washed twice with saturated saline (300 mL) and dried by addition of anhydrous sodium sulfate. The solvent was distilled away at reduced pressure, and the residue was purified by alumina column chromatography and recrystallized from ethanol. As a result, 4-(5,6,7-trifluoronaphthalen-2-yl)benzaldehyde (29.8 g) was obtained.

(3-3) 4-(5,6,7-Trifluoronaphthalen-2-yl)benzaldehyde (29.8 g) obtained in (3-2), water (30 mL), ethanol (150 mL), and THF (60 mL) were mixed and ice-cooled. Under cooling, sodium borohydride (1.2 g) was slowly added thereto, and the resulting mixture was stirred at room temperature for 2 hours. Under ice-cooling, a 6 mol % hydrochloric acid was slowly added, separation was conducted by adding dichloromethane (300 mL), dichloromethane (150 mL) was added to the aqueous layer to conduct extraction, and the combined organic layers were washed with water (300 mL) and saturated saline (300 mL), and dried by addition of anhydrous sodium sulfate. After the organic solvent was distilled away at a reduced pressure, the residue was recrystallized from a hexane-toluene mixed solvent to obtain 4-(5,6,7-trifluoronaphthalen-2-yl)benzyl alcohol (29.6 g).

The subsequent steps were the same as those of the methods described in Examples 1 and 2. As a result, trans-2-[4-(4-(3,4,5-trifluoronaphthalen-2-yl)benzyloxy)-3,5-difluorophenyl]-5-propyl-1,3-dioxane (11.1 g) was obtained.

MS m/z: 528 [M+]

¹HNMR (CDCl₃, TMS internal standard) δ (ppm)=8.05 (1H, d, J=8.7 Hz), 7.88 (1H, s), 7.75 (1H, d, j=8.7 Hz), 7.65 (2H, d, j=8.0 Hz), 7.56 (2H, d, j=8.0 Hz), 7.40-7.35 (1H, m), 6.70 (2H, d, j=8.5 Hz), 5.37 (1H, s), 5.17 (2H, s), 3.94-3.86 (4H, m), 2.62-2.48 (3H, m), 1.65-1.55 (2H, m), 0.92 (3H, t, J=7.4 Hz)

Example 4

Production of trans-5-(trans-4-propylcyclohexyl)-2-[4-(3,4-difluorobenzyloxy)-3,5-difluorophenyl]-1,3-dioxane (1a-49)

[Chem. 48]

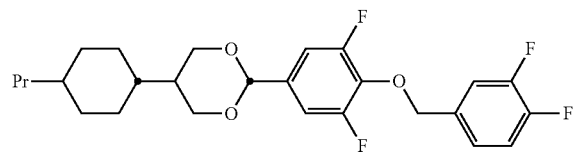

By the same method as those described in Examples 1 to 3, trans-5-(trans-4-propylcyclohexyl)-2-[4-(3,4-difluorobenzyloxy)-3,5-difluorophenyl]-1,3-dioxane was obtained.

MS m/z: 466 [M+]

$^1$HNMR(CDCl$_3$, TMS internal standard) δ (ppm)=7.31-7.27 (m, 1H), 7.24 (1H, dd, J1=2.0 Hz, J2=9.7 Hz), 7.21-7.17 (1H, m), 6.77 (2H, d, J=9.7 Hz), 5.36 (1H, s), 5.10 (2H, s), 4.25-4.21 (2H, m), 3.55-3.49 (2H, m), 2.48-2.42 (1H, m), 2.13-2.11 (1H, m), 1.90-1.84 (4H, m), 1.44-1.17 (7H, m), 1.08-0.97 (2H, m), 0.90 (3H, t, J=7.2 Hz)

Example 5

Production of trans-5-(trans-4-propylcyclohexyl)-2-[4-(4-(4-trifluoromethoxyphenyl)-3,5-difluorobenzyloxy)-3,5-difluorophenyl]-1,3-dioxane (1c-36)

[Chem. 49]

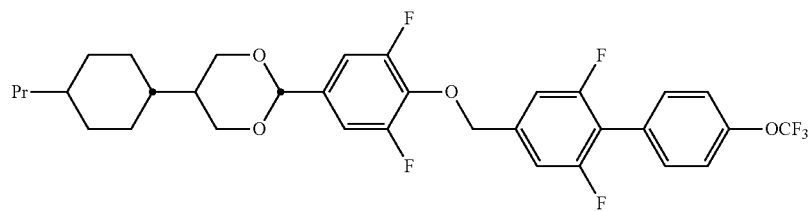

By the same method as those described in Examples 1 to 3, trans-5-(trans-4-propylcyclohexyl)-2-[4-(4-(4-trifluoromethoxyphenyl)-3,5-difluorobenzyloxy)-3,5-difluorophenyl]-1,3-dioxane was obtained.

MS m/z: 626 [M+]

$^1$HNMR (CDCl$_3$, TMS internal standard) δ (ppm)=7.49 (2H, d, J=8.6 Hz), 7.29 (2H, d, J=8.0 Hz), 6.86 (2H, d, J=9.0 Hz), 6.71 (2H, d, J=9.0 Hz), 5.36 (1H, s), 5.11 (2H, s), 4.24-4.21 (2H, m), 3.55-3.49 (2H, m), 2.48-2.42 (1H, m), 2.13-2.11 (1H, m), 1.90-1.84 (4H, m), 1.44-1.17 (7H, m), 1.07-0.99 (2H, m), 0.90 (3H, t, J=7.2 Hz)

Example 6

Production of trans-2-[4-(4-(5,6,7-trifluoronaphthalen-2-yl)benzyloxy)-3,5-difluorophenyl]-5-propyltetrahydropyran (1d-2)

[Chem. 50]

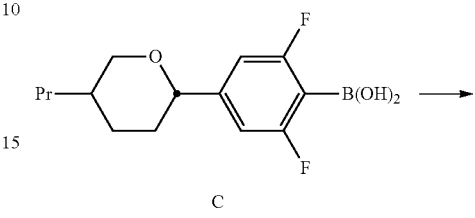

C

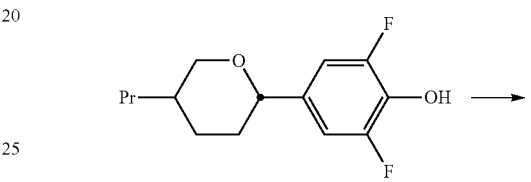

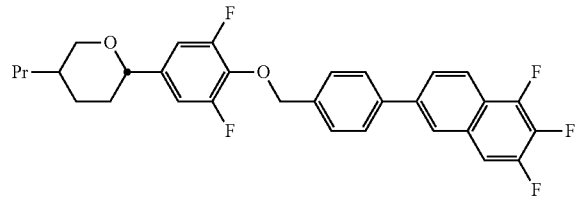

C was produced by a method described in a literature (Eur. J. Org. Chem. 2008, 3479-3487), and the subsequent steps were the same as those in Examples 1 to 3. As a result, trans-2-[4-(4-(5,6,7-trifluoronaphthalen-2-yl)benzyloxy)-3,5-difluorophenyl]-5-propyltetrahydropyran was obtained.

MS m/z: 526 [M+]

$^1$HNMR (CDCl$_3$, TMS internal standard) δ (ppm)=8.05 (1H, d, J=8.7 Hz), 7.88 (1H, s), 7.75 (1H, d, j=8.7 Hz), 7.65 (2H, d, j=8.0 Hz), 7.56 (2H, d, j=8.0 Hz), 7.40-7.35 (1H, m), 6.70 (2H, d, j=8.5 Hz), 5.17 (2H, s), 4.89-4.86 (1H, m), 3.54-3.35 (2H, m), 1.76-1.41 (9H, m), 0.90 (3H, t, J=7.2 Hz)

Example 7

Trans-2-[4-(4-(3,4,5-trifluorobenzyloxy)-3,5-difluorophenyl)phenyl]-5-propyl-1,3-dioxane (1a-14)

[Chem. 51]

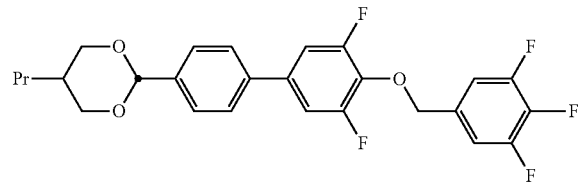

By the same method as those described in Examples 1 to 3, trans-2-[4-(4-(3,4,5-trifluorobenzyloxy)-3,5-difluorophenyl)phenyl]-5-propyl-1,3-dioxane was produced.

MS m/z: 478 [M+]

Phase transition temperature (° C.): Cr 89 X 110 SmA 125 N 146 Iso $^1$HNMR (CDCl$_3$, TMS internal standard) δ (ppm)=7.56 (2H, d, J=8.2 Hz), 7.50 (2H, d, 8.4 Hz), 7.16-7.10 (4H, m), 5.45 (1H, s), 5.10 (2H, s), 4.25 (2H, dd, J1=4.5 Hz, J2=11.7 Hz), 3.56 (2H, t, J=11.2 Hz), 2.19-2.13 (1H, m), 1.40-1.32 (2H, m), 1.13-1.07 (2H, m), 0.93 (3H, t, J=7.2 Hz)

Comparative Example 1

Production of [4-(trans-4-propylcyclohexyl)-2,6-difluorophenyloxy]-3,4,5-trifluorophenylmethane

[Chem. 52]

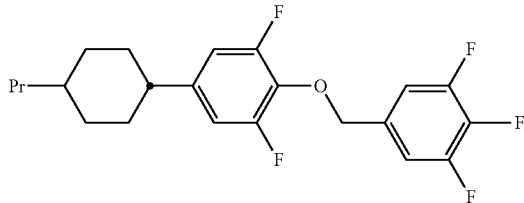

By a method described in WO 2012/161178, [4-(trans-4-propylcyclohexyl)-2,6-difluorophenyloxy]-3,4,5-trifluorophenylmethane was produced.

Comparative Example 2

Production of [4-(4-(trans-4-propylcyclohexyl)-2-fluorophenyl)-2,6-difluorophenyloxy]-3,4,5-trifluorophenylmethane

[Chem. 53]

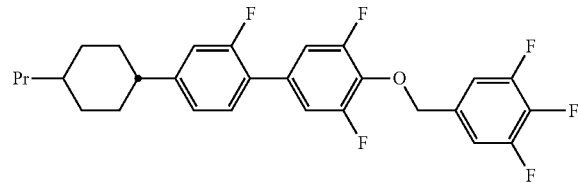

By a method described in WO 2012/161178, [4-(4-(trans-4-propylcyclohexyl)-2-fluoro)-2,6-difluorophenyloxy]-3,4,5-trifluorophenylmethane was produced.

Example 8

Preparation of Liquid Crystal Composition—1

A host liquid crystal composition (H) having the following composition was prepared.

[Chem. 54]

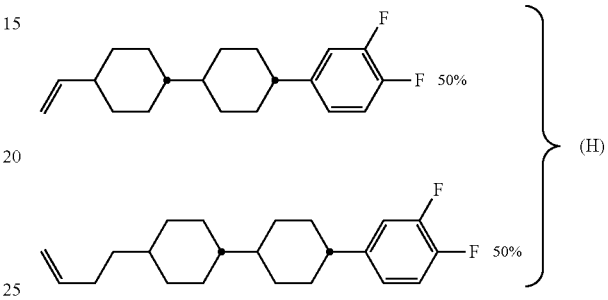

The physical properties of (H) were as follows.

Nematic phase upper limit temperature ($T_{n-i}$): 117.2° C.

Dielectric anisotropy (Δ∈): 4.38

Refractive index anisotropy (Δn): 0.0899

Viscosity ($\eta_{20}$): 20.3 mPa·s

A liquid crystal composition (M-A) containing 80% of this host liquid crystal (H) and 20% of trans-2-[4-(3,4,5-trifluorobenzyloxy)-3,5-difluorophenyl]-5-propyl-1,3-dioxane obtained in Example 1 was prepared. The physical properties of this composition were as follows.

$T_{n-i}$: 86.6° C.

Δ∈: 8.58

Δn: 0.0881

$\eta_{20}$: 22.0 mPa·s

The results show that the effect of adding trans-2-[4-(3,4,5-trifluorobenzyloxy)-3,5-difluorophenyl]-5-propyl-1,3-dioxane is to increase Δ∈ in positive (extrapolated Δ∈=25.4) without much increasing viscosity (extrapolated $\eta_{20}$=28.8 mPa·s). The prepared liquid crystal composition (M-A) maintained a homogeneous nematic liquid crystal state for 1 month or longer at room temperature.

Example 9

Preparation of liquid Crystal Composition—2

A liquid crystal composition (M-B) containing 80% of the host liquid crystal (H) and 20% of trans-2-[4-(4-(3,4,5-trifluorobenzyloxy)-3,5-difluorophenyl)-3-fluorophenyl]-5-propyl-1,3-dioxane obtained in Example 2 was prepared. The physical properties of this composition were as follows.

$T_{n-i}$: 109.4° C.

Δ∈: 9.18

Δn: 0.1015

$\eta_{20}$: 27.0 mPa·s

The results show that the effect of adding trans-2-[4-(4-(3,4,5-trifluorobenzyloxy)-3,5-difluorophenyl)-3-fluorophenyl]-5-propyl-1,3-dioxane is to increase Δ∈ in positive (extrapolated Δ∈=28.4) without much increasing viscosity (extrapolated $\eta_{20}$=53.8 mPa·s). The prepared liquid crystal composition (M-B) maintained a homogeneous nematic liquid crystal state for 1 month or longer at room temperature.

Example 10

Preparation of Liquid Crystal Composition—3

A liquid crystal composition (M-C) containing 80% of the host liquid crystal (H) and 20% of trans-2-[4-(4-(5,6,7-trifluoronaphthalen-2-yl)benzyloxy)-3,5-difluorophenyl]-5-propyl-1,3-dioxane obtained in Example 3 was prepared. The physical properties of this composition were as follows.

$T_{n-i}$: 114.5° C.
$\Delta\epsilon$: 10.73
$\Delta n$: 0.1118
$\eta_{20}$: 29.7 mPa·s The results show that the effect of adding trans-2-[4-(4-(5,6,7-trifluoronaphthalen-2-yl)benzyloxy)-3,5-difluorophenyl]-5-propyl-1,3-dioxane is to increase $\Delta\epsilon$ in positive (extrapolated $\Delta\epsilon$=36.1) without much increasing viscosity (extrapolated $\eta_{20}$=67.3 mPa·s). The prepared liquid crystal composition (M-C) maintained a homogeneous nematic liquid crystal state for 1 month or longer at room temperature.

Comparative Example 3

Preparation of Liquid Crystal Composition—4

A liquid crystal composition (M-D) containing 80% of the host liquid crystal (H) and 20% of [4-(trans-4-propylcyclohexyl)-2,6-difluorophenyloxy]-3,4,5-trifluorophenylmethane obtained in Comparative Example 1 was prepared. The physical properties of this composition were as follows.

$T_{n-i}$: 89.0° C.
$\Delta\epsilon$: 6.54
$\Delta n$: 0.0856
$\eta_{20}$: 18.6 mPa·s The extrapolated $\Delta\epsilon$ was 15.2 and the extrapolated $\eta_{20}$ was 11.8 mPa·s when [4-(trans-4-propylcyclohexyl)-2,6-difluorophenyloxy]-3,4,5-trifluorophenylmethane was added.

Comparative Example 4

Preparation of Liquid Crystal Composition—5

A liquid crystal composition (M-E) containing 80% of the host liquid crystal (H) and 20% of [4-(4-(trans-4-propylcyclohexyl)-2-fluorophenyl)-2,6-difluorophenyloxy]-3,4,5-trifluorophenylmethane obtained in Comparative Example 2 was prepared. The physical properties of this composition were as follows.

$T_{n-i}$: 115.8° C.
$\Delta\epsilon$: 7.67
$\Delta n$: 0.0996
$\eta_{20}$: 24.7 mPa·s The extrapolated $\Delta\epsilon$ was 20.8 and the extrapolated $\eta_{20}$ was 42.3 mPa·s when[4-(4-(trans-4-propylcyclohexyl)-2-fluorophenyl)-2,6-difluorophenyloxy]-3,4,5-trifluorophenylmethane was added.

Example 8 and Comparative Example 3 are compared. Whereas the extrapolated $\Delta\epsilon$ of Comparative Example 3 was 15.2, the extrapolated $\Delta\epsilon$ of Example 8 was 25.4, which is large. Whereas the extrapolated viscosity ($\eta_{20}$) of Comparative Example 3 was 11.8 mPa·s, the extrapolated viscosity ($\eta_{20}$) of Example 8 was 28.8 mPa·s and did not show a large increase compared to Comparative Example 3.

Example 9 and Comparative Example 4 are compared. Whereas the extrapolated $\Delta\epsilon$ of Comparative Example 4 was 20.8, the extrapolated $\Delta\epsilon$ of Example 9 was 28.4, which is large. Whereas the extrapolated viscosity ($\eta_{20}$) of Comparative Example 4 was 42.3 mPa·s, the extrapolated viscosity ($\eta_{20}$) of Example 9 was 53.8 mPa·s and did not show a large increase compared to Comparative Example 4.

The results described above demonstrate that the compound of the present application shows large $\Delta\epsilon$ without significantly degrading viscosity and maintains high miscibility with other liquid crystal compounds.

The invention claimed is:

1. A compound represented by general formula (1)

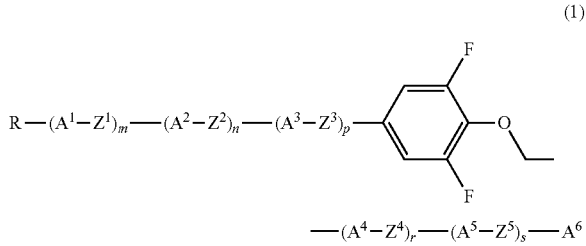

(where R represents an alkyl group having 1 to 15 carbon atoms or an alkenyl group having 2 to 15 carbon atoms and one —$CH_2$— or two or more non-adjacent —$CH_2$— in the group may each be substituted with —O—, —S—, —COO—, —OCO—, or —CO—, $A^1$, $A^2$, $A^3$, $A^4$, and $A^5$ each independently represent a group selected from the group consisting of (a) a 1,4-cyclohexylene group (one —$CH_2$— or two or more non-adjacent —$CH_2$— in the group may each be substituted with —O— or —S—), (b) a 1,4-phenylene group (one —CH= or two or more non-adjacent —CH= in the group may each be substituted with —N= and a hydrogen atom in the group may be substituted with a fluorine atom), and (c) a naphthalene-2,6-diyl group (a hydrogen atom in the group may be substituted with a fluorine atom), at least one group selected from $A^1$, $A^2$, and $A^3$ is a group represented by

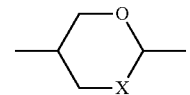

(where X represents an oxygen atom), $Z^1$, $Z^2$, $Z^3$, $Z^4$, and $Z^5$ each independently represent —$CH_2O$—, —$OCH_2$—, —$CF_2O$—, —$OCF_2$—, —$CH_2CH_2$—, —$CF_2CF_2$—, —CH=CH—, —CF=CF—, —C≡C—, or a single bond, $A^6$ represents

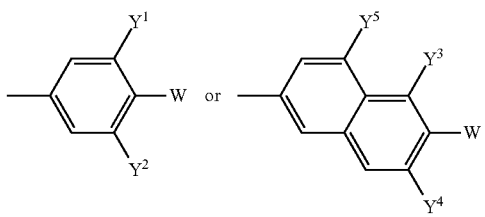

(where W represents a fluorine atom, a chlorine atom, a cyano group, —CF$_3$, —OCH$_2$F, —OCHF$_2$, or —OCF$_3$, and $Y^1$, $Y^3$, $Y^4$, and $Y^5$ each independently represent a fluorine atom, a chlorine atom, or a hydrogen atom), and m, n, p, r, and s each independently represent 0 or 1, at least one selected from m, n, and p represents 1, m+n+p+r+s equals 1, 2, or 3, and at least one group selected from $A^1$, $A^2$, and $A^3$ corresponding to m, n, and p representing 1 is

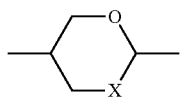

(where X represents an oxygen atom)).

2. The compound according to claim 1, wherein, $A^1$, $A^2$, $A^3$, $A^4$, and $A^5$ in general formula (1) each independently represent a group selected from below:

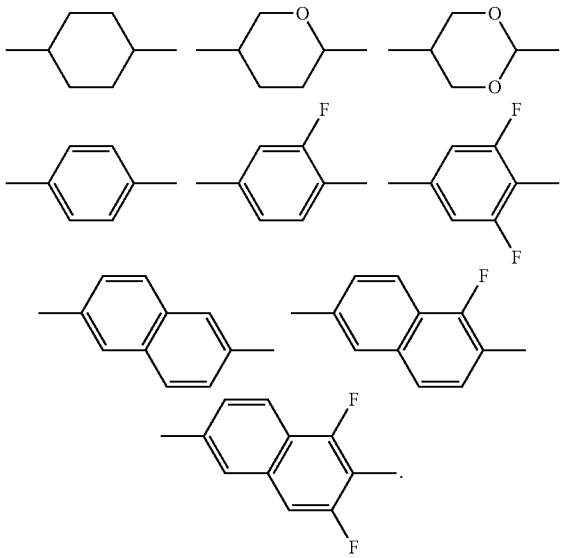

3. The compound according to claim 1, wherein $Z^1$, $Z^2$, $Z^3$, $Z^4$, and $Z^5$ in general formula (1) each independently represent —OCH$_2$—, —CF$_2$O—, —CH$_2$CH$_2$—, —C≡C—, or a single bond.

4. The compound according to claim 1, wherein W in general formula (1) represents a fluorine atom, a cyano group, or —OCF$_3$.

5. The compound according to claim 1, wherein $A^6$ in general formula (1) represents below:

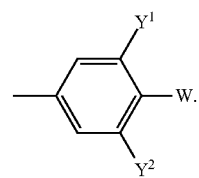

6. The compound according to claim 1, wherein $A^6$ in general formula (1) represents below:

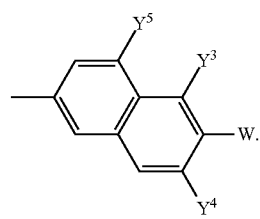

7. The compound according to claim 1, wherein the compound is a compound selected from compounds represented by general formula (1a) to general formula (1f):

(1a)

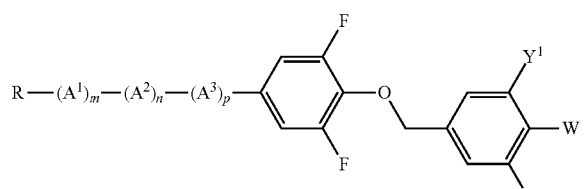

(1b)

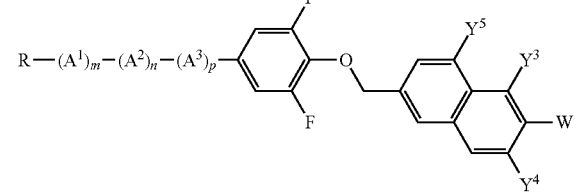

(1c)

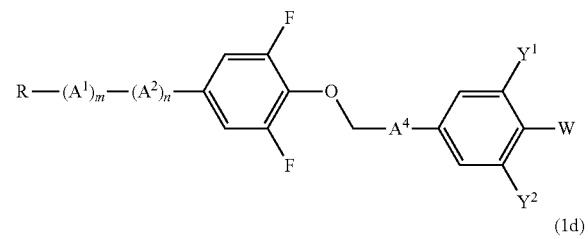

(1d)

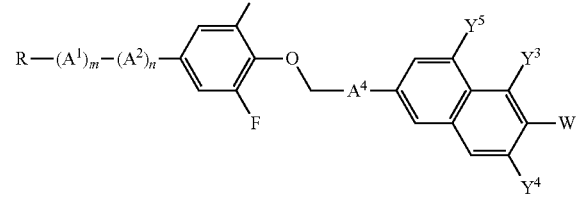

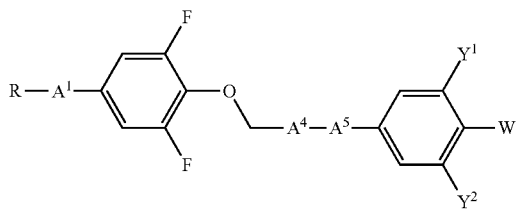 (1e)

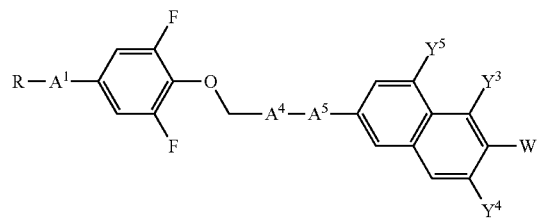 (1f)

(where R, W, $Y^1$, $Y^2$, $Y^3$, $Y^4$, and $Y^5$ are respectively the same as R, W, $Y^1$, $Y^2$, $Y^3$, $Y^4$, and $Y^5$ in general formula (1), $A^1$, $A^2$, $A^3$, $A^4$, and $A^6$ each independently represent a group selected from the group consisting of (a) a 1,4-cyclohexylene group (one —$CH_2$— or two or more non-adjacent —$CH_2$— in the group may each be substituted with —O— or —S—) and (b) a 1,4-phenylene group (one —CH═ or two or more non-adjacent —CH═ in the group may each be substituted with —N═ and a hydrogen atom in the group may be substituted with a fluorine atom), at least one group selected from $A^1$, $A^2$ and $A^3$ is

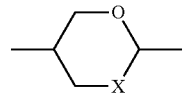

(where X represents an oxygen atom), in general formula (1a) and general formula (1b), m, n, and p each independently represent 0 or 1 and at least one selected from m, n, and p represents 1, and in general formula (1c) and general formula (1d), m and n each independently represent 0 or 1 and at least one selected from m and n represents 1).

8. A liquid crystal composition comprising one or more compounds according to claim 1.

9. A liquid crystal display device that uses the liquid crystal composition according to claim 8.

* * * * *